(12) United States Patent
Wells et al.

(10) Patent No.: US 11,034,774 B2
(45) Date of Patent: Jun. 15, 2021

(54) ENGINEERED ANTIBODIES FOR THE DETECTION OF PHOSPHORYLATED TYROSINE

(71) Applicant: The Regents of the University of California, Oakland, CA (US)

(72) Inventors: James Wells, Burlingame, CA (US); Yun Mou, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/669,458

(22) Filed: Oct. 30, 2019

(65) Prior Publication Data

US 2020/0131277 A1     Apr. 30, 2020

Related U.S. Application Data

(60) Provisional application No. 62/752,345, filed on Oct. 30, 2018.

(51) Int. Cl.
    *C07K 16/44*          (2006.01)
    *C07K 16/18*          (2006.01)

(52) U.S. Cl.
    CPC .............. *C07K 16/44* (2013.01); *C07K 16/18* (2013.01); *C07K 2317/32* (2013.01); *C07K 2317/40* (2013.01); *C07K 2317/565* (2013.01); *C07K 2318/20* (2013.01)

(58) Field of Classification Search
    CPC .... C07K 16/18; C07K 16/44; C07K 2318/20; C07K 2317/24; C07K 2317/32; C07K 2317/40; C07K 2317/55; C07K 2317/565; C07K 2317/92
See application file for complete search history.

(56) References Cited

U.S. PATENT DOCUMENTS 6,824,989 B1   11/2004   Eisinger et al.
6,870,034 B2    3/2005   Breece

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Ruff-Jamison et al., "Heavy and Light Chain Variable Region Ssequence and Antibody Properties of Anti-phosphotyrosine Antibodies Reveal Both Common and Distinct Features," The Journal of Biological Chemistry, vol. 266, No. 10, Issue of Apr. 5, 1991, pp. 6607-6613.
Carter et al., "Humanization of an Anti-p185(HER2) Antibody for Human Cancer Therapy," Proc. Natl. Acad. Sci, vol. 89, pp. 4285-4289, May 1992.
Glenney, Jr., et al., "Monoclonal Antibodies to Phosphotyrosine," Journal of Immunological Methods, 109 (1988) pp. 277-285.

* cited by examiner

*Primary Examiner* — Robert S Landsman

(57) ABSTRACT

Presented herein are novel phosphotyrosine binding compositions, including antibodies and antibody fragments. The inventors of the present disclosure have resolved the crystal structures of two widely utilized pan-specific pY antibodies, PY20 and 4G10. These two known antibodies, although developed independently from animal immunizations, have surprisingly similar modes of recognition of the phosphate group, and revealed a generic binding structure among pan-specific pY antibodies. Based on this newly discovered convergent structure, engineered CDR-L3 loops were developed that impart greatly improved affinity to pY binding antibodies and other pY binding compositions. The inventions disclosed herein include antibodies and antibody fragments bearing these novel CDR-L3 sequences and methods of using such pY binding compositions for the detection of phosphotyrosine-bearing proteins.

12 Claims, 10 Drawing Sheets

Specification includes a Sequence Listing.

CDR-L3

```
        CDR-L3
PY2   88-CQQ(T)SKVPWT-97       SEQ ID NO: 44
PY20  88-CQQ(T)SKVPWT-97       SEQ ID NO: 45
PY42  88-CEQ(N)TFPRT-97        SEQ ID NO: 46
PY54  88-CQQ(T)SKVPWT-97       SEQ ID NO: 47
PY69  88-CQQ(S)KLPWT-97        SEQ ID NO: 48
129   88-CQQ(G)TSYPYT-97       SEQ ID NO: 49
4G10  88-CQQ(S)G(Y)FF-98       SEQ ID NO: 50
              *
```

CDR-H2

```
        CDR-H2
PY2   52-(I)NPNSFGTN-60        SEQ ID NO: 51
PY20  52-(I)NPNSGGTR-58        SEQ ID NO: 52
PY42  52-(I)NPNTGTI-58         SEQ ID NO: 53
PY54  52-(I)NPNSHGTN-60        SEQ ID NO: 54
PY69  52-(I)NPNSGGST-58        SEQ ID NO: 55
129   52-(I)NPNNGTS-58         SEQ ID NO: 56
4G10  52-(P)YYGGSI-58          SEQ ID NO: 57
              ***       *
```

CDR-H1

```
        CDR-H1
PY2   26-GYTFTEYI(IH)W-36      SEQ ID NO: 58
PY20  26-GYTFTEY(TMH)W-36      SEQ ID NO: 59
PY42  26-GYTFTEY(TMH)W-36      SEQ ID NO: 60
PY54  26-GYTFTEYI(IH)W-36      SEQ ID NO: 61
PY69  26-GYTFTEY(TMH)W-36      SEQ ID NO: 62
129   26-GYTFTEY(TMH)W-36      SEQ ID NO: 63
4G10  26-GYTFTTEY(TMH)W-36     SEQ ID NO: 64
```

CDR-H3

```
        CDR-H3
PY2   95-(R)RD-----NL(Y)FDYW-103   SEQ ID NO: 65
PY20  95-(R)PYGNYYNS(Y)FDYW-103    SEQ ID NO: 66
PY42  95-(R)GR-----EY(H)MDYW-103   SEQ ID NO: 67
PY54  95-(R)RD-----NL(Y)FDYW-103   SEQ ID NO: 68
PY69  95-(R)PYGNYYTS(Y)FDYW-103    SEQ ID NO: 69
129   95-(R)NLITTVV--AKSPDYW-103   SEQ ID NO: 70
4G10  95-(R)AG-----A(Y)FDYW-103    SEQ ID NO: 71
                         **
```

* Water binding
** Phosphate binding
*** GG Motif for the pY-proceeding residue binding

FIG. 3

|  | CDR-L1 | CDR-L2 | CDR-L3 |
|---|---|---|---|
| PY20ᴬᴰˢ | ITCSASQGISNYLNWYQ SEQ ID NO: 72 | LIYYTSSLHSGVP SEQ ID NO: 74 | CQQYSKVPWTFG SEQ ID NO: 76 |
| 4G10ᴬᴰˢ | ITCRASSVSSSYLHWYQ SEQ ID NO: 73 | LIYSTSNLASGVP SEQ ID NO: 75 | CQQYSGYRTFG SEQ ID NO: 77 |

|  | CDR-H1 | CDR-H2 |  |
|---|---|---|---|
| PY20ᴬᴰˢ | ASGYTFTEYTMHWV SEQ ID NO: 78 | LEWMGGINPNSGGTRDNQRFKGK | SEQ ID NO: 80 |
| 4G10ᴬᴰˢ | ASGYTFTENTVHWV SEQ ID NO: 79 | LEWIGGINPYYGGSIFSPKFKGK | SEQ ID NO: 81 |

|  | CDR-H3 |  |
|---|---|---|
| PY20ᴬᴰˢ | CARRGPYGNYYNSYYFDYW | SEQ ID NO: 82 |
| 4G10ᴬᴰˢ | CARRAGAYYFDYW | SEQ ID NO: 83 |

*FIG. 4* hu4D5 DIQMTQSPSSLSASVGDRVTITCRASQDVNTAVAWYQQKPGKAPKLLIYSASFLYSGVPSRFS hu4D5 GSRSGTDFTLTISSLQPEDFATYYCQQHYTTPPTFGQGTKVEIKR  SEQ ID NO: 84 hu4D5 EVQLVESGGGLVQPGGSLRLSCAASGFNIKDTYIHWVRQAPGKGLEWVARIYPTNGYTRY hu4D5 ADSVKGRFTISADTSKNTAYLQMNSLRAEDTAVYYCSRWGGDGFYAMDYWGQGTLVTVSS

SEQ ID NO: 85

Motif 1:
XX(T/S)S
SEQ ID NO: 89

Motif 2:
XXXG
SEQ ID NO: 86

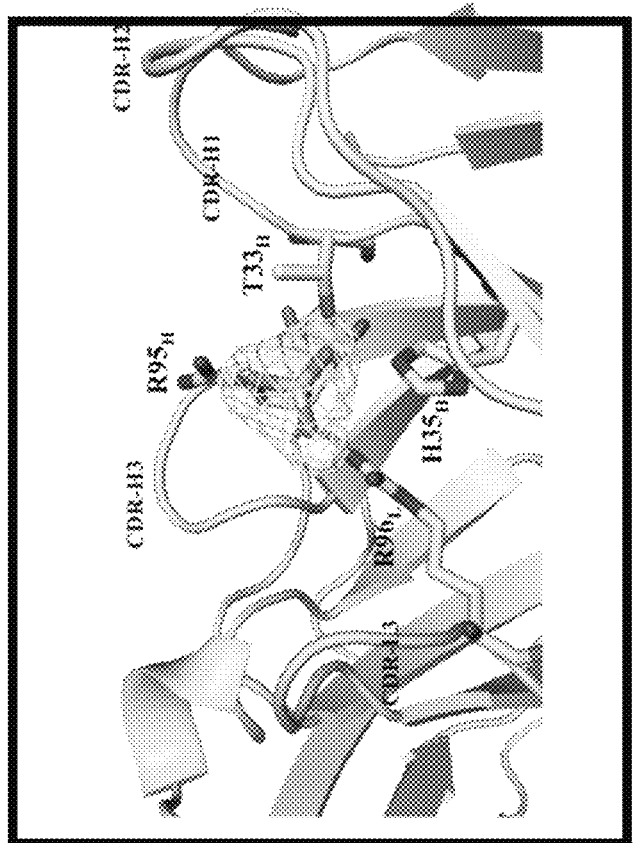
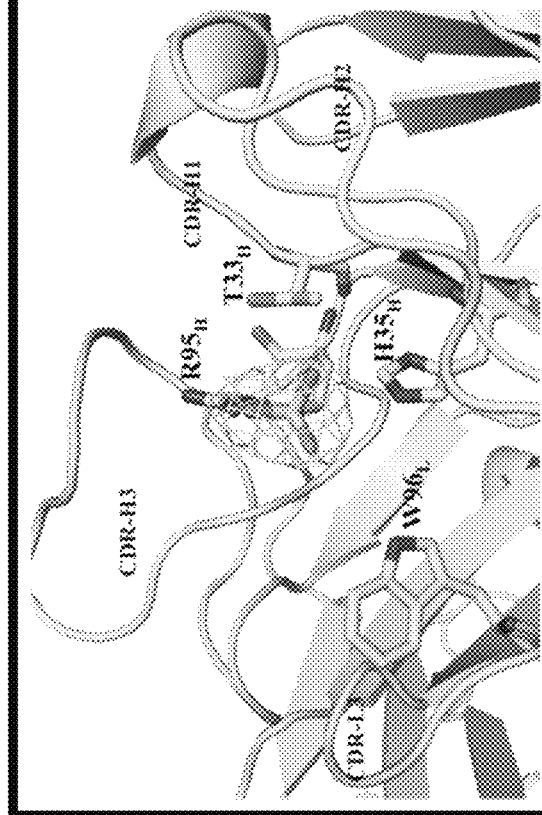
Fig. 7A
Fig. 7B

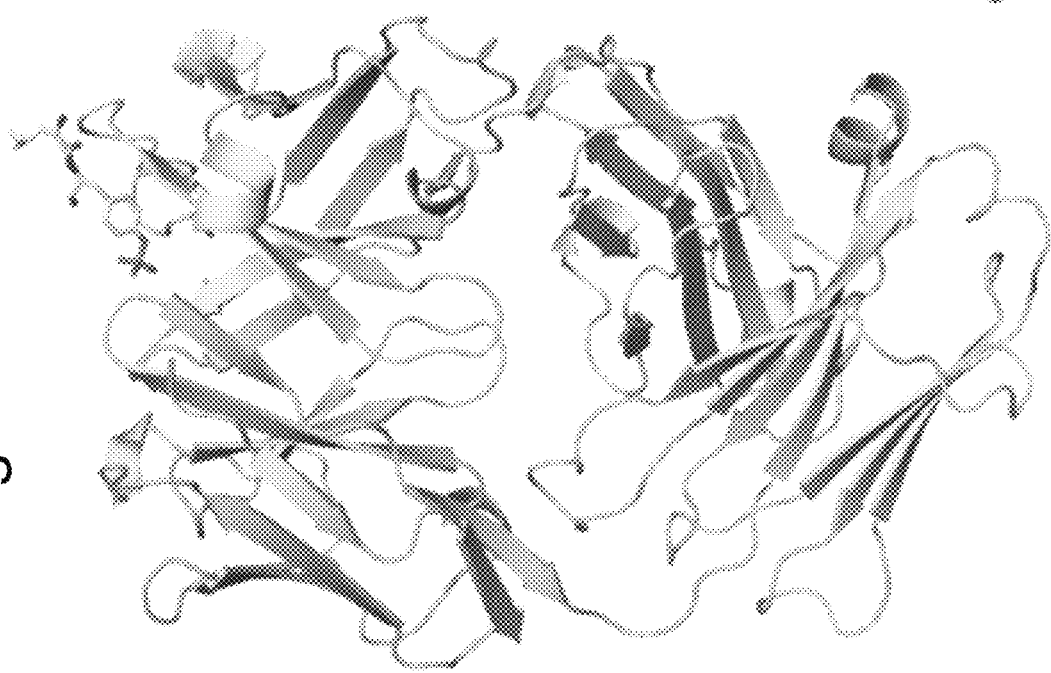
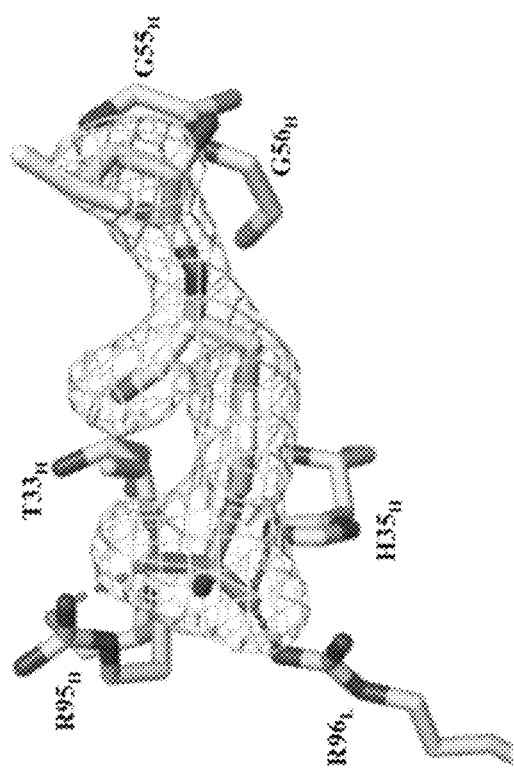
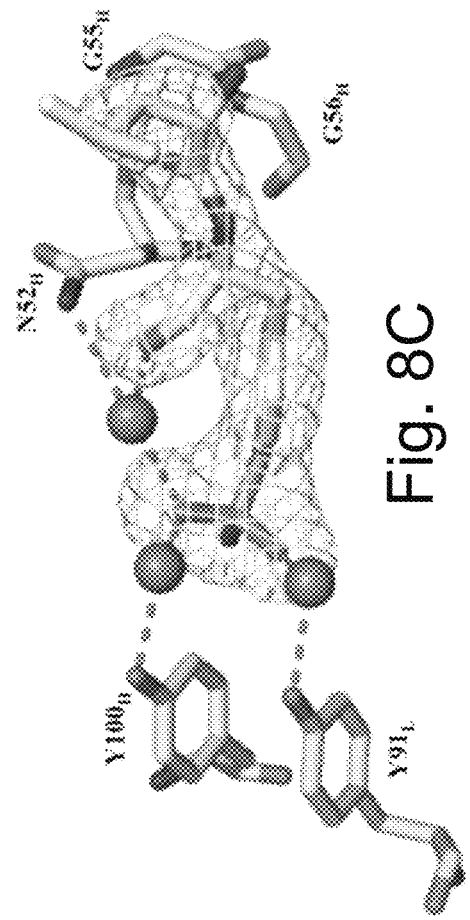

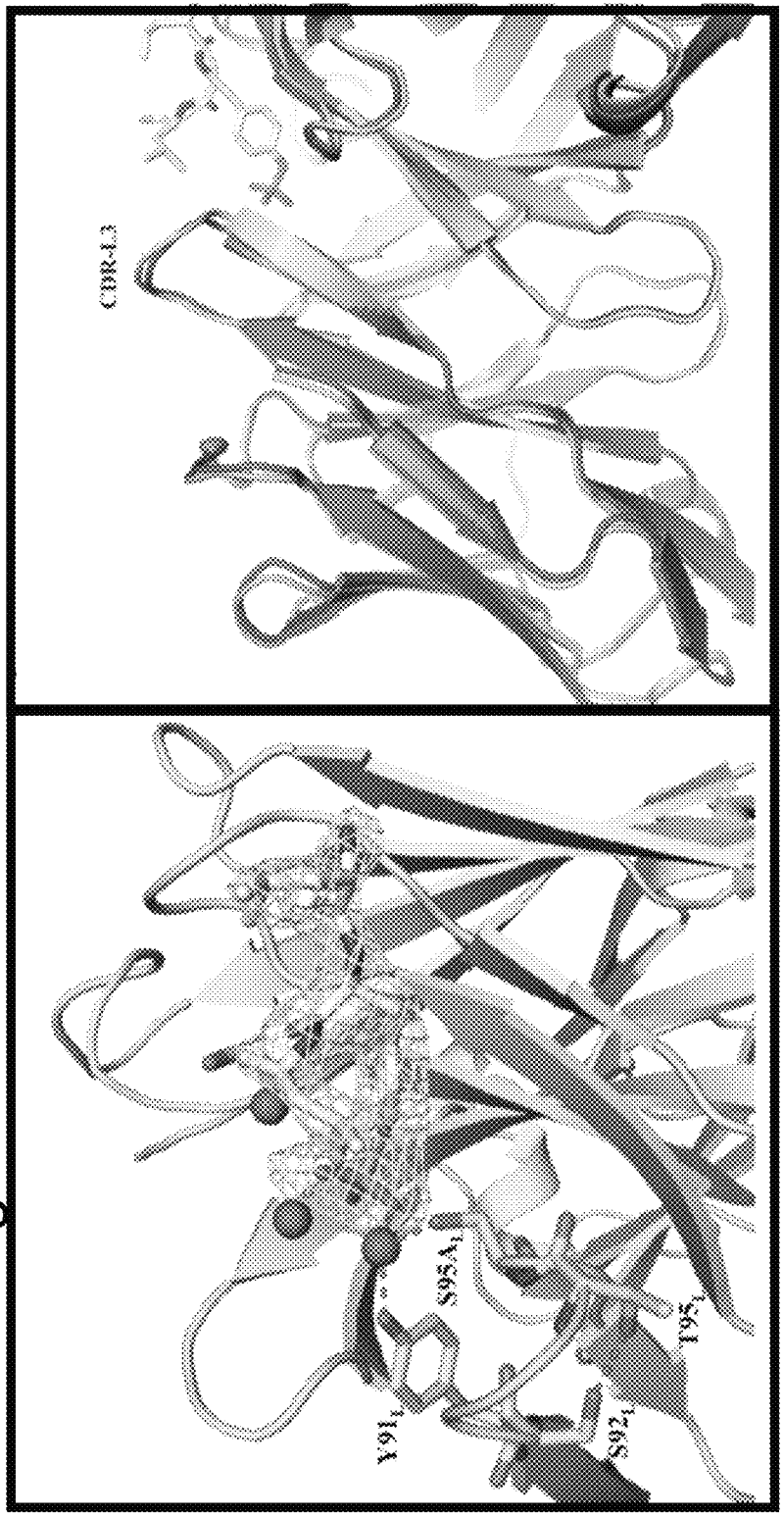

US 11,034,774 B2

SEQUENCE LISTING

```
<160> NUMBER OF SEQ ID NOS: 105

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      engineered CDR L3 sequence
<220> FEATURE:
<221> NAME/KEY: MOD_RES
<222> LOCATION: (3)..(12)
<223> OTHER INFORMATION: Any amino acid
<220> FEATURE:
<221> NAME/KEY: MISC_FEATURE
<222> LOCATION: (3)..(12)
<223> OTHER INFORMATION: This region may encompass 2-10 residues
<220> FEATURE:
<223> OTHER INFORMATION: See specification as filed for detailed
      description of substitutions and preferred embodiments

<400> SEQUENCE: 1

Tyr Ser Xaa Xaa Xaa Xaa Xaa Xaa Xaa Xaa Xaa Xaa Tyr Arg
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      engineered CDR L3 sequence
<220> FEATURE:
<221> NAME/KEY: MOD_RES
<222> LOCATION: (1)..(2)
<223> OTHER INFORMATION: Any amino acid

<400> SEQUENCE: 2

Xaa Xaa Thr Ser
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      engineered CDR L3 sequence
<220> FEATURE:
<221> NAME/KEY: MOD_RES
<222> LOCATION: (1)..(2)
<223> OTHER INFORMATION: Any amino acid

<400> SEQUENCE: 3

Xaa Xaa Ser Ser
1

<210> SEQ ID NO 4
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      engineered CDR L3 sequence
<220> FEATURE:
<221> NAME/KEY: MOD_RES
<222> LOCATION: (1)..(3)
<223> OTHER INFORMATION: Any amino acid

<400> SEQUENCE: 4

Xaa Xaa Xaa Gly
1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      4G10 CDR L3 sequence

<400> SEQUENCE: 5

Tyr Ser Gly Tyr Arg
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 6

Tyr Ser Pro Trp Thr Ser Tyr Arg
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 7

Tyr Ser Arg His Thr Ser Tyr Arg
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 8

Tyr Ser Arg Ser Ser Ser Tyr Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
``` engineered CDR L3 sequence

<400> SEQUENCE: 9

Tyr Ser Arg Leu Thr Ser Tyr Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 10

Tyr Ser Arg Arg Thr Ser Tyr Arg
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 11

Tyr Ser Ser Arg Thr Ser Tyr Arg
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 12

Tyr Ser Ser Arg Lys Gly Tyr Arg
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 13

Tyr Ser Ala Gly Met Gly Tyr Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 14

Tyr Ser Gly Arg Tyr Gly Tyr Arg
1               5

<210> SEQ ID NO 15

```
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 15

Tyr Ser Arg Pro Tyr Gly Tyr Arg
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 16

Tyr Ser Arg Tyr Lys Gly Tyr Arg
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 17

Tyr Ser Arg Pro Trp Gly Tyr Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 18

Tyr Ser Ser Arg Lys Gly Tyr Arg
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 19

Tyr Ser Gly Arg Tyr Gly Tyr Arg
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 20
```

Tyr Ser Arg Pro Tyr Gly Tyr Arg
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 21

Tyr Ser Arg Tyr Lys Gly Tyr Arg
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 22

Tyr Ser Arg Pro Trp Gly Tyr Arg
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      engineered CDR L3 sequence

<400> SEQUENCE: 23

Tyr Ser Arg Arg Thr Ser Tyr Arg
1               5

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      4G10 Light Chain CDR 1 (L1) sequence

<400> SEQUENCE: 24

Arg Ala Ser Ser Ser Val Ser Ser Ser Tyr Leu His
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      4G10 Light Chain CDR 2 (L2) sequence

<400> SEQUENCE: 25

Ser Thr Ser Asn Leu Ala Ser
1               5

<210> SEQ ID NO 26
<211> LENGTH: 8
<212> TYPE: PRT
<213> ORGANISM: Artificial Sequence
<220> FEATURE:

```
<223> OTHER INFORMATION: Description of Artificial Sequence: Synthetic
      4G10 Heavy Chain CDR 1 (H1) sequence

<400> SEQUENCE: 26

Tyr Thr Phe Thr Glu Asn Thr Val
1               5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      4G10 Heavy Chain CDR 2 (H2) sequence

<400> SEQUENCE: 27

Ile Gly Gly Ile Asn Pro Tyr Tyr Gly Gly Ser Ile Phe Ser Pro Lys
1               5                   10                  15

Phe

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      4G10 Heavy Chain CDR 3 (H3) sequence

<400> SEQUENCE: 28

Arg Ala Gly Ala Tyr Tyr Phe
1               5

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      PY20 Light Chain CDR 1 (L1) sequence

<400> SEQUENCE: 29

Ser Ala Ser Gln Gly Ile Ser Asn Tyr Leu Asn
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      PY20 Light Chain CDR 2 (L2) sequence

<400> SEQUENCE: 30

Tyr Thr Ser Ser Leu His Ser
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      PY20 Heavy Chain CDR 1 (H1) sequence

<400> SEQUENCE: 31

Tyr Thr Phe Thr Glu Tyr Thr Met
1               5
```

```
<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      PY20 Heavy Chain CDR 2 (H2) sequence

<400> SEQUENCE: 32

Met Gly Gly Ile Asn Pro Asn Ser Gly Gly Thr Arg Asp Asn Gln Arg
1               5                   10                  15

Phe

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      PY20 Heavy Chain CDR 3 (H3) sequence

<400> SEQUENCE: 33

Arg Gly Pro Tyr Gly Asn Tyr Tyr Asn Ser Tyr Tyr Phe
1               5                   10

<210> SEQ ID NO 34
<211> LENGTH: 454
<212> TYPE: PRT
<213> ORGANISM: Artificial Sequence
<220> FEATURE:
<223> OTHER INFORMATION: Description of Artificial Sequence: Synthetic
      4G10 antibody heavy chain

<400> SEQUENCE: 34

Glu Val Gln Leu Gln Gln Ser Gly Pro Glu Leu Val Lys Pro Gly Ala
1               5                   10                  15

Ser Val Met Ile Ser Cys Arg Thr Ser Ala Tyr Thr Phe Thr Glu Asn
            20                  25                  30

Thr Val His Trp Val Lys Gln Ser His Gly Glu Ser Leu Glu Trp Ile
        35                  40                  45

Gly Gly Ile Asn Pro Tyr Tyr Gly Gly Ser Ile Phe Ser Pro Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Ala Gly Ala Tyr Tyr Phe Asp Tyr Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Ser Val His Thr Phe Pro Ala Leu Leu Gln
                165                 170                 175

Ser Gly Leu Tyr Thr Met Ser Ser Ser Val Thr Val Pro Ser Ser Thr
            180                 185                 190

Trp Pro Ser Gln Thr Val Thr Cys Ser Val Ala His Pro Ala Ser Ser
```

```
            195                 200                 205
Thr Thr Val Asp Lys Lys Leu Glu Pro Ser Gly Pro Ile Ser Thr Ile
    210                 215                 220
Asn Pro Cys Pro Pro Cys Lys Glu Cys His Lys Cys Pro Ala Pro Asn
225                 230                 235                 240
Leu Glu Gly Gly Pro Ser Val Phe Ile Phe Pro Pro Asn Ile Lys Asp
                245                 250                 255
Val Leu Met Ile Ser Leu Thr Pro Lys Val Thr Cys Val Val Val Asp
                260                 265                 270
Val Ser Glu Asp Asp Pro Asp Val Gln Ile Ser Trp Phe Val Asn Asn
            275                 280                 285
Val Glu Val His Thr Ala Gln Thr Gln Thr His Arg Glu Asp Tyr Asn
            290                 295                 300
Ser Thr Ile Arg Val Val Ser Thr Leu Pro Ile Gln His Gln Asp Trp
305                 310                 315                 320
Met Ser Gly Lys Glu Phe Lys Cys Lys Val Asn Asn Lys Asp Leu Pro
                325                 330                 335
Ser Pro Ile Glu Arg Thr Ile Ser Lys Ile Lys Gly Leu Val Arg Ala
            340                 345                 350
Pro Gln Val Tyr Ile Leu Pro Pro Pro Ala Glu Gln Leu Ser Arg Lys
            355                 360                 365
Asp Val Ser Leu Thr Cys Leu Val Val Gly Phe Asn Pro Gly Asp Ile
370                 375                 380
Ser Val Glu Trp Thr Ser Asn Gly His Thr Glu Glu Asn Tyr Lys Asp
385                 390                 395                 400
Thr Ala Pro Val Leu Asp Ser Asp Gly Ser Tyr Phe Ile Tyr Ser Lys
                405                 410                 415
Leu Asn Met Lys Thr Ser Lys Trp Glu Lys Thr Asp Ser Phe Ser Cys
            420                 425                 430
Asn Val Arg His Glu Gly Leu Lys Asn Tyr Tyr Leu Lys Lys Thr Ile
            435                 440                 445
Ser Arg Ser Pro Gly Lys
            450

<210> SEQ ID NO 35
<211> LENGTH: 209
<212> TYPE: PRT
<213> ORGANISM: Artificial Sequence
<220> FEATURE:
<223> OTHER INFORMATION: Description of Artificial Sequence: Synthetic
      4G10 antibody light chain with grafted CDR-L3
<220> FEATURE:
<221> NAME/KEY: NON_CONS
<222> LOCATION: (91)..(92)
<223> OTHER INFORMATION: Residues at these positions are separated by a
      CDR-L3 sequence

<400> SEQUENCE: 35

Glu Asn Val Leu Thr Gln Ser Pro Ala Ile Met Ser Ala Ser Pro Gly
1               5                   10                  15
Glu Lys Val Thr Met Thr Cys Arg Ala Ser Ser Ser Val Ser Ser Ser
            20                  25                  30
Tyr Leu His Trp Tyr Arg Gln Lys Ser Gly Ala Ser Pro Lys Leu Trp
        35                  40                  45
Ile Tyr Ser Thr Ser Asn Leu Ala Ser Gly Val Pro Ala Arg Phe Ser
    50                  55                  60
Gly Ser Gly Ser Gly Thr Ser Tyr Ser Leu Thr Ile Ser Ser Val Glu
```

```
                65                  70                  75                  80
Ala Glu Asp Ala Ala Thr Tyr Tyr Cys Gln Gln Thr Phe Gly Gly Gly
                    85                  90                  95

Thr Lys Leu Glu Ile Lys Arg Ala Asp Ala Ala Pro Thr Val Ser Ile
            100                 105                 110

Phe Pro Pro Ser Ser Glu Gln Leu Thr Ser Gly Gly Ala Ser Val Val
            115                 120                 125

Cys Phe Leu Asn Asn Phe Tyr Pro Arg Asp Ile Asn Val Lys Trp Lys
            130                 135                 140

Ile Asp Gly Ser Glu Arg Gln Asn Gly Val Leu Asn Ser Trp Thr Asp
145                 150                 155                 160

Gln Asp Ser Lys Asp Ser Thr Tyr Ser Met Ser Ser Thr Leu Thr Leu
            165                 170                 175

Thr Lys Asp Glu Tyr Glu Arg His Asn Ser Tyr Thr Cys Glu Ala Thr
            180                 185                 190

His Lys Thr Ser Thr Ser Pro Ile Val Lys Ser Phe Asn Arg Asn Glu
            195                 200                 205

Cys
```

<210> SEQ ID NO 36
<211> LENGTH: 217
<212> TYPE: PRT
<213> ORGANISM: Artificial Sequence
<220> FEATURE:
<223> OTHER INFORMATION: Description of Artificial Sequence: Synthetic
      4G10 antibody light chain with grafted G4 CDR-L3

<400> SEQUENCE: 36

```
Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Arg Gln Lys Ser Gly Ala Ser Pro Lys Leu Trp
            35                  40                  45

Ile Tyr Ser Thr Ser Asn Leu Ala Ser Gly Val Pro Ala Arg Phe Ser
50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Arg Pro Tyr
                85                  90                  95

Gly Tyr Arg Thr Phe Gly Gly Thr Lys Leu Glu Ile Lys Arg Ala
            100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
            130                 135                 140

Arg Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
            165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
            195                 200                 205

Val Lys Ser Phe Asn Arg Asn Glu Cys
```

<210> SEQ ID NO 37
<211> LENGTH: 217
<212> TYPE: PRT
<213> ORGANISM: Artificial Sequence
<220> FEATURE:
<223> OTHER INFORMATION: Description of Artificial Sequence: Synthetic
    4G10 antibody light chain with grafted G6 CDR-L3

<400> SEQUENCE: 37

```
Glu Asn Val Leu Thr Gln Ser Pro Ala Ile Met Ser Ala Ser Pro Gly
1               5                   10                  15

Glu Lys Val Thr Met Thr Cys Arg Ala Ser Ser Val Ser Ser Ser
            20                  25                  30

Tyr Leu His Trp Tyr Arg Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Arg Pro Trp
                85                  90                  95

Gly Tyr Arg Thr Phe Gly Gly Gly Thr Lys Leu Glu Ile Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
130                 135                 140

Arg Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215
```

<210> SEQ ID NO 38
<211> LENGTH: 190
<212> TYPE: PRT
<213> ORGANISM: Artificial Sequence
<220> FEATURE:
<223> OTHER INFORMATION: Description of Artificial Sequence: Synthetic
    4D5 antibody light chain with selectable grafted CDRL-1,
    CDR-L2, and CDR-L3 sequences
<220> FEATURE:
<221> NAME/KEY: NON_CONS
<222> LOCATION: (23)..(24)
<223> OTHER INFORMATION: Residues at these positions are separated by a
    CDR-L1 sequence
<220> FEATURE:
<221> NAME/KEY: NON_CONS
<222> LOCATION: (38)..(39)
<223> OTHER INFORMATION: Residues at these positions are separated by a
    CDR-L2 sequence
<220> FEATURE:
<221> NAME/KEY: NON_CONS
<222> LOCATION: (72)..(73)
<223> OTHER INFORMATION: Residues at these positions are separated by a
    CDR-L3 sequence

<400> SEQUENCE: 38

```
Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Arg
        35                  40                  45

Ser Gly Thr Asp Phe Thr Leu Thr Ile Ser Ser Leu Gln Pro Glu Asp
50                  55                  60

Phe Ala Thr Tyr Tyr Cys Gln Gln Thr Phe Gly Gln Gly Thr Lys Val
65                  70                  75                  80

Glu Ile Lys Arg Thr Val Ala Ala Pro Ser Val Phe Ile Phe Pro Pro
                85                  90                  95

Ser Asp Glu Gln Leu Lys Ser Gly Thr Ala Ser Val Val Cys Leu Leu
            100                 105                 110

Asn Asn Phe Tyr Pro Arg Glu Ala Lys Val Gln Trp Lys Val Asp Asn
        115                 120                 125

Ala Leu Gln Ser Gly Asn Ser Gln Glu Ser Val Thr Glu Gln Asp Ser
130                 135                 140

Lys Asp Ser Thr Tyr Ser Leu Ser Ser Thr Leu Thr Leu Ser Lys Ala
145                 150                 155                 160

Asp Tyr Glu Lys His Lys Val Tyr Ala Cys Glu Val Thr His Gln Gly
                165                 170                 175

Leu Ser Ser Pro Val Thr Lys Ser Phe Asn Arg Gly Glu Cys
            180                 185                 190
```

<210> SEQ ID NO 39
<211> LENGTH: 209
<212> TYPE: PRT
<213> ORGANISM: Artificial Sequence
<220> FEATURE:
<223> OTHER INFORMATION: Description of Artificial Sequence: Synthetic
      4D5 antibody light chain with grafted 4G10 CDRL-1 and CDR-L2
      sequences, and selectable grafted CDR-L3 sequence
<220> FEATURE:
<221> NAME/KEY: NON_CONS
<222> LOCATION: (91)..(92)
<223> OTHER INFORMATION: Residues at these positions are separated by a
      CDR-L3 sequence

<400> SEQUENCE: 39

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Thr Phe Gly Gln Gly
                85                  90                  95

Thr Lys Val Glu Ile Lys Arg Thr Val Ala Ala Pro Ser Val Phe Ile
            100                 105                 110

Phe Pro Pro Ser Asp Glu Gln Leu Lys Ser Gly Thr Ala Ser Val Val
        115                 120                 125
```

```
Cys Leu Leu Asn Asn Phe Tyr Pro Arg Glu Ala Lys Val Gln Trp Lys
        130                 135                 140

Val Asp Asn Ala Leu Gln Ser Gly Asn Ser Gln Glu Ser Val Thr Glu
145                 150                 155                 160

Gln Asp Ser Lys Asp Ser Thr Tyr Ser Leu Ser Ser Thr Leu Thr Leu
                165                 170                 175

Ser Lys Ala Asp Tyr Glu Lys His Lys Val Tyr Ala Cys Glu Val Thr
            180                 185                 190

His Gln Gly Leu Ser Ser Pro Val Thr Lys Ser Phe Asn Arg Gly Glu
        195                 200                 205

Cys

<210> SEQ ID NO 40
<211> LENGTH: 217
<212> TYPE: PRT
<213> ORGANISM: Artificial Sequence
<220> FEATURE:
<223> OTHER INFORMATION: Description of Artificial Sequence: Synthetic
      4D5 antibody light chain with grafted 4G10 CDRL-1
      and CDR-L2 sequences, and grafted G4 CDR-L3 sequence

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Ser Arg Pro Tyr
                85                  90                  95

Gly Tyr Arg Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 41
<211> LENGTH: 217
<212> TYPE: PRT
<213> ORGANISM: Artificial Sequence
<220> FEATURE:
<223> OTHER INFORMATION: Description of Artificial Sequence: Synthetic
```

4D5 antibody light chain with grafted 4G10 CDRL-1
and CDR-L2 sequences, and grafted G6 CDR-L3 sequence

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Ser Arg Pro Trp
                85                  90                  95

Gly Tyr Arg Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 42
<211> LENGTH: 416
<212> TYPE: PRT
<213> ORGANISM: Artificial Sequence
<220> FEATURE:
<223> OTHER INFORMATION: Description of Artificial Sequence: Synthetic
      4D5 antibody heavy chain with grafted selectable CDR-H1,
      CDR-H2, and CDR-H3 sequences
<220> FEATURE:
<221> NAME/KEY: NON_CONS
<222> LOCATION: (26)..(27)
<223> OTHER INFORMATION: Residues at these positions are separated by a
      CDR-H1 sequence
<220> FEATURE:
<221> NAME/KEY: NON_CONS
<222> LOCATION: (39)..(40)
<223> OTHER INFORMATION: Residues at these positions are separated by a
      CDR-H2 sequence
<220> FEATURE:
<221> NAME/KEY: NON_CONS
<222> LOCATION: (73)..(74)
<223> OTHER INFORMATION: Residues at these positions are separated by a
      CDR-H3 sequence

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly His Trp Val Arg Gln Ala
            20                  25                  30

```
Pro Gly Lys Gly Leu Glu Trp Lys Gly Lys Phe Thr Ile Ser Ala Asp
            35                  40                  45

Thr Ser Lys Asn Thr Ala Tyr Leu Gln Met Asn Ser Leu Arg Ala Glu
 50                  55                  60

Asp Thr Ala Val Tyr Tyr Cys Ala Arg Asp Tyr Trp Gly Gln Gly Thr
 65                  70                  75                  80

Leu Val Thr Val Ser Ser Ala Ser Thr Lys Gly Pro Ser Val Phe Pro
                     85                  90                  95

Leu Ala Pro Ser Ser Lys Ser Thr Ser Gly Gly Thr Ala Ala Leu Gly
                100                 105                 110

Cys Leu Val Lys Asp Tyr Phe Pro Glu Pro Val Thr Val Ser Trp Asn
                115                 120                 125

Ser Gly Ala Leu Thr Ser Gly Val His Thr Phe Pro Ala Val Leu Gln
130                 135                 140

Ser Ser Gly Leu Tyr Ser Leu Ser Ser Val Val Thr Val Pro Ser Ser
145                 150                 155                 160

Ser Leu Gly Thr Gln Thr Tyr Ile Cys Asn Val Asn His Lys Pro Ser
                165                 170                 175

Asn Thr Lys Val Asp Lys Lys Val Glu Pro Lys Ser Cys Asp Lys Thr
                180                 185                 190

His Thr Cys Pro Pro Cys Pro Ala Pro Glu Leu Leu Gly Gly Pro Ser
                195                 200                 205

Val Phe Leu Phe Pro Pro Lys Pro Lys Asp Thr Leu Met Ile Ser Arg
210                 215                 220

Thr Pro Glu Val Thr Cys Val Val Val Asp Val Ser His Glu Asp Pro
225                 230                 235                 240

Glu Val Lys Phe Asn Trp Tyr Val Asp Gly Val Glu Val His Asn Ala
                245                 250                 255

Lys Thr Lys Pro Arg Glu Glu Gln Tyr Asn Ser Thr Tyr Arg Val Val
                260                 265                 270

Ser Val Leu Thr Val Leu His Gln Asp Trp Leu Asn Gly Lys Glu Tyr
                275                 280                 285

Lys Cys Lys Val Ser Asn Lys Ala Leu Pro Ala Pro Ile Glu Lys Thr
                290                 295                 300

Ile Ser Lys Ala Lys Gly Gln Pro Arg Glu Pro Gln Val Tyr Thr Leu
305                 310                 315                 320

Pro Pro Ser Arg Glu Glu Met Thr Lys Asn Gln Val Ser Leu Thr Cys
                325                 330                 335

Leu Val Lys Gly Phe Tyr Pro Ser Asp Ile Ala Val Glu Trp Glu Ser
                340                 345                 350

Asn Gly Gln Pro Glu Asn Asn Tyr Lys Thr Thr Pro Pro Val Leu Asp
                355                 360                 365

Ser Asp Gly Ser Phe Phe Leu Tyr Ser Lys Leu Thr Val Asp Lys Ser
370                 375                 380

Arg Trp Gln Gln Gly Asn Val Phe Ser Cys Ser Val Met His Glu Ala
385                 390                 395                 400

Leu His Asn His Tyr Thr Gln Lys Ser Leu Ser Leu Ser Pro Gly Lys
                405                 410                 415

<210> SEQ ID NO 43
<211> LENGTH: 448
<212> TYPE: PRT
<213> ORGANISM: Artificial Sequence
<220> FEATURE:
```

<223> OTHER INFORMATION: Description of Artificial Sequence: Synthetic
     4D5 antibody heavy chain with grafted 4G10 CDR-H1, CDR-H2,
     and CDR-H3 sequences

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Glu Asn
            20                  25                  30

Thr Val His Trp Val Arg Gln Ala Pro Gly Lys Gly Leu Glu Trp Ile
        35                  40                  45

Gly Gly Ile Asn Pro Tyr Tyr Gly Gly Ser Ile Phe Ser Pro Lys Phe
    50                  55                  60

Lys Gly Lys Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ala Tyr Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp

```
385                 390                 395                 400
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      PY2 antibody CDR-L3 alignment sequence

<400> SEQUENCE: 44

Cys Gln Gln Tyr Ser Lys Val Pro Trp Thr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      PY20 antibody CDR-L3 alignment sequence

<400> SEQUENCE: 45

Cys Gln Gln Tyr Ser Lys Val Pro Trp Thr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      PY42 antibody CDR-L3 alignment sequence

<400> SEQUENCE: 46

Cys Glu Gln His Asn Thr Thr Pro Arg Thr
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      PY54 antibody CDR-L3  alignment sequence

<400> SEQUENCE: 47

Cys Gln Gln Tyr Ser Lys Val Pro Trp Thr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      PY69 antibody CDR-L3 alignment sequence

<400> SEQUENCE: 48

Cys Gln Gln Tyr Ser Lys Leu Pro Trp Thr
```

-continued

```
<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      129 antibody CDR-L3 alignment sequence

<400> SEQUENCE: 49

Cys Gly Gln Gly Tyr Ser Tyr Pro Tyr Thr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      4G10 antibody CDR-L3 alignment sequence

<400> SEQUENCE: 50

Cys Gln Gln Tyr Ser Gly Tyr Arg Thr Phe
1               5                   10

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      PY2 antibody CDR-H2 alignment sequence

<400> SEQUENCE: 51

Asn Pro Asn Ser Gly Gly Thr Asn
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      PY20 antibody CDR- H2 alignment sequence

<400> SEQUENCE: 52

Asn Pro Asn Ser Gly Gly Thr Arg
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      PY42 antibody CDR- H2 alignment sequence

<400> SEQUENCE: 53

Asn Pro Asn Thr Gly Gly Thr Ile
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
```

PY54 antibody CDR- H2 alignment sequence

<400> SEQUENCE: 54

Asn Pro Asn Ser Gly Gly Thr Asn
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      PY69 antibody CDR- H2 alignment sequence

<400> SEQUENCE: 55

Asn Pro Asn Ser Gly Gly Ser Thr
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      129 antibody CDR- H2 alignment sequence

<400> SEQUENCE: 56

Asn Pro Asn Asn Gly Gly Thr Ser
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      4G10 antibody CDR- H2 alignment sequence

<400> SEQUENCE: 57

Asn Pro Tyr Tyr Gly Gly Ser Ile
1               5

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      PY2 antibody CDR-H1 alignment sequence

<400> SEQUENCE: 58

Gly Tyr Thr Phe Thr Glu Tyr Ile Ile His Trp
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      PY20 antibody CDR- H1 alignment sequence

<400> SEQUENCE: 59

Gly Tyr Thr Phe Thr Glu Tyr Thr Met His Trp
1               5                   10

<210> SEQ ID NO 60

```
<211> LENGTH: 11
<212> TYPE: PRT
<213> ORGANISM: Artificial Sequence
<220> FEATURE:
<223> OTHER INFORMATION: Description of Artificial Sequence: Synthetic
      PY42 antibody CDR- H1 alignment sequence

<400> SEQUENCE: 60

Gly Tyr Thr Phe Thr Glu Tyr Thr Ile His Trp
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      PY54 antibody CDR- H1  alignment sequence

<400> SEQUENCE: 61

Gly Tyr Thr Phe Thr Glu Tyr Ile Ile His Trp
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      PY69 antibody CDR- H1 alignment sequence

<400> SEQUENCE: 62

Gly Tyr Thr Phe Thr Glu Tyr Thr Met His Trp
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      129 antibody CDR- H1 alignment sequence

<400> SEQUENCE: 63

Gly Tyr Thr Phe Thr Glu Tyr Thr Met His Trp
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      4G10 antibody CDR- H1 alignment sequence

<400> SEQUENCE: 64

Gly Tyr Thr Phe Thr Glu Asn Thr Val His Trp
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      PY2 antibody CDR-H3 alignment sequence

<400> SEQUENCE: 65
```

Arg Gly Asp Asn Leu Tyr Tyr Phe Asp Tyr Trp
1               5                   10

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      PY20 antibody CDR- H3 alignment sequence

<400> SEQUENCE: 66

Arg Gly Pro Tyr Gly Asn Tyr Tyr Asn Ser Tyr Tyr Phe Asp Tyr Trp
1               5                   10                  15

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      PY42 antibody CDR- H3 alignment sequence

<400> SEQUENCE: 67

Arg Gly Arg Glu Tyr Thr Met Asp Tyr Trp
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      PY54 antibody CDR- H3  alignment sequence

<400> SEQUENCE: 68

Arg Gly Asp Asn Leu Tyr Tyr Phe Asp Tyr Trp
1               5                   10

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      PY69 antibody CDR- H3 alignment sequence

<400> SEQUENCE: 69

Arg Gly Pro Tyr Gly Asn Tyr Tyr Thr Ser Tyr Tyr Phe Asp Tyr Trp
1               5                   10                  15

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      129 antibody CDR- H3 alignment sequence

<400> SEQUENCE: 70

Arg Gly Leu Thr Thr Val Val Ala Lys Ser Phe Asp Tyr Trp
1               5                   10

<210> SEQ ID NO 71
<211> LENGTH: 10
<212> TYPE: PRT
<213> ORGANISM: Artificial Sequence
<220> FEATURE:

```
<223> OTHER INFORMATION: Description of Artificial Sequence: Synthetic
      4G10 antibody CDR- H3 alignment sequence

<400> SEQUENCE: 71

Arg Ala Gly Ala Tyr Tyr Phe Asp Tyr Trp
1               5                   10

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      PY204D5 CDR-L1 and flanking sequence

<400> SEQUENCE: 72

Ile Thr Cys Ser Ala Ser Gln Gly Ile Ser Asn Tyr Leu Asn Trp Tyr
1               5                   10                  15

Gln

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      4G104D5 CDR-L1 and flanking sequence

<400> SEQUENCE: 73

Ile Thr Cys Arg Ala Ser Ser Ser Val Ser Ser Ser Tyr Leu His Trp
1               5                   10                  15

Tyr Gln

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      PY204D5 CDR-L2 and flanking sequence

<400> SEQUENCE: 74

Leu Ile Tyr Tyr Thr Ser Ser Leu His Ser Gly Val Pro
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      4G104D5 CDR-L2 and flanking sequence

<400> SEQUENCE: 75

Leu Ile Tyr Ser Thr Ser Asn Leu Ala Ser Gly Val Pro
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      PY204D5 CDR-L3 and flanking sequence

<400> SEQUENCE: 76
```

Cys Gln Gln Tyr Ser Lys Val Pro Trp Thr Phe Gly
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      4G104D5 CDR-L3 and flanking sequence

<400> SEQUENCE: 77

Cys Gln Gln Tyr Ser Gly Tyr Arg Thr Phe Gly
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      PY204D5 CDR-H1 and flanking sequence

<400> SEQUENCE: 78

Ala Ser Gly Tyr Thr Phe Thr Glu Tyr Thr Met His Trp Val
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      4G104D5 CDR-H1 and flanking sequence

<400> SEQUENCE: 79

Ala Ser Gly Tyr Thr Phe Thr Glu Asn Thr Val His Trp Val
1               5                   10

<210> SEQ ID NO 80
<211> LENGTH: 23
<212> TYPE: PRT
<213> ORGANISM: Artificial Sequence
<220> FEATURE:
<223> OTHER INFORMATION: Description of Artificial Sequence: Synthetic
      PY204D5 CDR-H2 and flanking sequence

<400> SEQUENCE: 80

Leu Glu Trp Met Gly Gly Ile Asn Pro Asn Ser Gly Gly Thr Arg Asp
1               5                   10                  15

Asn Gln Arg Phe Lys Gly Lys
            20

<210> SEQ ID NO 81
<211> LENGTH: 23
<212> TYPE: PRT
<213> ORGANISM: Artificial Sequence
<220> FEATURE:
<223> OTHER INFORMATION: Description of Artificial Sequence: Synthetic
      4G104D5 CDR-H2 and flanking sequence

<400> SEQUENCE: 81

Leu Glu Trp Ile Gly Gly Ile Asn Pro Tyr Tyr Gly Gly Ser Ile Phe
1               5                   10                  15

Ser Pro Lys Phe Lys Gly Lys
            20

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      PY204D5 CDR-H3 and flanking sequence

<400> SEQUENCE: 82

Cys Ala Arg Arg Gly Pro Tyr Gly Asn Tyr Tyr Asn Ser Tyr Tyr Phe
1               5                   10                  15

Asp Tyr Trp

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence: Synthetic
      4G104D5 CDR-H3 and flanking sequence

<400> SEQUENCE: 83

Cys Ala Arg Arg Ala Gly Ala Tyr Tyr Phe Asp Tyr Trp
1               5                   10

<210> SEQ ID NO 84
<211> LENGTH: 108
<212> TYPE: PRT
<213> ORGANISM: Artificial Sequence
<220> FEATURE:
<223> OTHER INFORMATION: Description of Artificial Sequence: Synthetic
      4D5 light chain variable region sequence

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105

<210> SEQ ID NO 85
<211> LENGTH: 120
<212> TYPE: PRT
<213> ORGANISM: Artificial Sequence
<220> FEATURE:
<223> OTHER INFORMATION: Description of Artificial Sequence: Synthetic
      4D5 heavy chain variable region sequence

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

-continued

```
Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      Py binding motif 2
<220> FEATURE:
<221> NAME/KEY: MOD_RES
<222> LOCATION: (1)..(3)
<223> OTHER INFORMATION: Any amino acid

<400> SEQUENCE: 86

Xaa Xaa Xaa Gly
1

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      Gly pY sequence
<220> FEATURE:
<221> NAME/KEY: MOD_RES
<222> LOCATION: (4)..(4)
<223> OTHER INFORMATION: phospho-Tyr

<400> SEQUENCE: 87

Gly Gly Gly Tyr Gly Gly Gly
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      GlyY sequence

<400> SEQUENCE: 88

Gly Gly Gly Tyr Gly Gly Gly
1               5

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Synthetic
      pY Binding Motif 1
<220> FEATURE:
<221> NAME/KEY: MOD_RES
<222> LOCATION: (1)..(2)
```

```
<223> OTHER INFORMATION: Any amino acid
<220> FEATURE:
<221> NAME/KEY: MOD_RES
<222> LOCATION: (3)..(3)
<223> OTHER INFORMATION: Thr or Ser

<400> SEQUENCE: 89

Xaa Xaa Xaa Ser
1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
      Mutant 4G10 CDR-L3 Insertion S1 sequence

<400> SEQUENCE: 90

Pro Trp Thr Ser
1

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
      Mutant 4G10 CDR-L3 Insertion S2 sequence

<400> SEQUENCE: 91

Arg His Thr Ser
1

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
      Mutant 4G10 CDR-L3 Insertion S3 sequence

<400> SEQUENCE: 92

Arg Ser Ser Ser
1

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Synthetic
      Mutant 4G10 CDR-L3 Insertion S4 sequence

<400> SEQUENCE: 93

Arg Leu Thr Ser
1

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
      Mutant 4G10 CDR-L3 Insertion S5 sequence

<400> SEQUENCE: 94

Arg Arg Thr Ser
```

```
<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Synthetic
      Mutant 4G10 CDR-L3 Insertion S6 sequence

<400> SEQUENCE: 95

Ser Arg Thr Ser
1

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
      Mutant 4G10 CDR-L3 Insertion G1 sequence

<400> SEQUENCE: 96

Ser Arg Lys Gly
1

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Synthetic
      Mutant 4G10 CDR-L3 Insertion G2 sequence

<400> SEQUENCE: 97

Ala Gly Met Gly
1

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic
      Mutant 4G10 CDR-L3 Insertion G3 sequence

<400> SEQUENCE: 98

Gly Arg Tyr Gly
1

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      Mutant 4G10 CDR-L3 Insertion G4 sequence

<400> SEQUENCE: 99

Arg Pro Tyr Gly
1

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Synthetic
```

Mutant 4G10 CDR-L3 Insertion G5 sequence

<400> SEQUENCE: 100

Arg Tyr Lys Gly
1

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Synthetic
      Mutant 4G10 CDR-L3 Insertion G6 sequence

<400> SEQUENCE: 101

Arg Pro Trp Gly
1

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      1i8i pY sequence
<220> FEATURE:
<221> NAME/KEY: MOD_RES
<222> LOCATION: (11)..(11)
<223> OTHER INFORMATION: phospho-Tyr

<400> SEQUENCE: 102

Gly Glu Lys Lys Gly Asn Tyr Val Val Thr Tyr Ala
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      1i8i pS sequence
<220> FEATURE:
<221> NAME/KEY: MOD_RES
<222> LOCATION: (11)..(11)
<223> OTHER INFORMATION: phospho-Ser

<400> SEQUENCE: 103

Gly Glu Lys Lys Gly Asn Tyr Val Val Thr Ser Ala
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      1i8i pT sequence
<220> FEATURE:
<221> NAME/KEY: MOD_RES
<222> LOCATION: (11)..(11)
<223> OTHER INFORMATION: phospho-Thr

<400> SEQUENCE: 104

Gly Glu Lys Lys Gly Asn Tyr Val Val Thr Thr Ala
1               5                   10

<210> SEQ ID NO 105
<211> LENGTH: 6
<212> TYPE: PRT

```
<213> ORGANISM: Artificial Sequence
<220> FEATURE:
<223> OTHER INFORMATION: Description of Artificial Sequence: Synthetic
      6xHis tag

<400> SEQUENCE: 105

His His His His His His
1               5
```

ENGINEERED ANTIBODIES FOR THE DETECTION OF PHOSPHORYLATED TYROSINE

CROSS-REFERENCE TO RELATED APPLICATIONS

This application claims the benefit of priority to U.S. Provisional Patent Application Ser. No. 62/752,345 entitled "Engineered Antibodies for the Detection of Phosphorylated Tyrosine," filed Oct. 30, 2018, the contents of which are hereby incorporated by reference.

STATEMENT REGARDING FEDERALLY SPONSORED RESEARCH OR DEVELOPMENT

This invention was made with government support under grant number P41 CA196276 awarded by the National Institutes of Health. The government has certain rights in the invention.

The instant application contains a Sequence Listing which has been submitted electronically in ASCII format and is hereby incorporated by reference in its entirety. Said ASCII copy, created on Apr. 6, 2021, is named UCSF070NP_SL.txt and is 54,339 bytes in size.

BACKGROUND OF THE INVENTION

Phosphotyrosine (pY) is a critical posttranslational modification (PTM) that modulates numerous signaling events in eukaryotes, including growth factor signaling, cell differentiation, and T-cell activation. Due to their pervasive roles in cell biology, the dysregulation of pY PTMs has been implicated in many human diseases, such as neurodegeneration and cancer. Collectively, there have been more than 44,000 non-redundant pY sites discovered in human and mouse according to PhosphoSitePlus, and the number is steadily growing along with the advances of pY proteomic technologies. Together with hundreds of pY kinases and phosphatases, understanding the complex network of pY regulation is a significant challenge in the post-genome era.

Unlike the other two common phosphorylation PTMs (pS and pT) that are relatively abundant in cells, pY is far less abundant (approximately 0.1% or less of all phosphorylation PTMs). Studying pY PTMs, therefore, requires very specific and sensitive probes. During the last two decades, many antibodies or pY binding domains have been developed to pan-specifically isolate pY PTMs with varying degrees of success. Improving the sensitivity and specificity of these probes is still highly desirable. Structure-guided mutagenesis combined with binding selections has been applied to generate sequence specific and recombinant antibodies for pS and pT, but not yet for pY. Key to these studies was the use of structure-guided phage display from a structurally defined scaffold to focus mutations leading to improvement in pS and pT binding affinities for both the phosphorylation state and sequence. Despite a long history of developing and employing pY antibodies in many applications (Western blot, immunofluorescence, proteomics, etc.), the structural mechanism of how the antibodies recognize the pY group remains unknown.

Accordingly, there is a need in the art for improved pan-specific pY antibodies having improved binding properties, stability, and other performance characteristics. Relatedly, there is a need in the art for understanding the structural factors that facilitate pY antibody binding to phosphotyrosine targets, which would enable the design of improved binders of pY.

SUMMARY OF THE INVENTION

Herein are disclosed novel antibody CDR sequences which greatly improve pY binding affinity of pan-Py antibodies and other pY binding compositions. The improved sequences were developed based on the novel resolution of the crystal structures of two widely utilized pan-specific pY antibodies, PY20 and 4G10. Although generated independently from animal immunizations, surprisingly, the mode of molecular recognition of the pY group is highly conserved between the two antibodies. Both structures host a deeply buried cationic binding site for the phosphate group that provides multiple hydrogen bonds and salt bridges from the same residues in the antibodies. The tyrosine extends the phosphate group to the binding site without $\pi$-$\pi$ stacking or cation-$\pi$ interactions with the antibody that would not accommodate pS or pT. Based on these newly discovered convergent structural features, the inventors of the present disclosure further optimized binding affinity with the aid of computational design and phage display selection. These disclosures provide the art with multiple novel CDR sequences which may be utilized in any number of antibodies, antibody fragments, or other protein binders. These disclosures provide the art with pY binding compositions with high affinity and superior performance.

BRIEF DESCRIPTION OF THE DRAWINGS

FIG. 3 depicts sequence alignments of pY antibodies. The sequence alignments reveal that PY2, PY20, PY42, PY54, PY69, 129, and 4G10 share similar pY binding modes as the critical binding residues are conserved.

FIG. 4 depicts humanization of PY20 and 4G10 onto the 4D5 scaffold. The six CDRs from PY20 and 4G10 (underlined) were grafted onto the 4D5 scaffold (only flanking regions of the CDRs are shown), resulting in the chimeric PY20$^{4D5}$ and 4G10$^{4D5}$.

FIG. 6A depicts motif 1, having the XX(T/S)S sequence (SEQ ID NO: 89), and FIG. 6B depicts motif 2 having the XXXG sequence (SEQ ID NO: 86) at the CDR-L3 insertions.

FIG. 7A: crystal structure PY20$^{4D5}$/sulfate complex structure. Two residues from CDR-H1 (T33$_H$, H35$_H$) and one residue from CDR-H3 (R95$_H$) form hydrogen bonds or salt bridges to the sulfate ion. FIG. 7B: 4G10$^{4D5}$/sulfate complex crystal structure. 4G10$^{4D5}$ uses the same three residues as PY20$^{4D5}$ to bind the sulfate ion with an additional binding residue R96$_L$ from CDR-L3. The omit map (Fo-Fc) of the sulfate group is shown at the 3a contour level in both figures.

FIGS. 8A, 8B and 8C. Crystal structure of 4G10$^{4D5}$/LpYL peptide complex shows a complementary H-bonding binding site for binding pY. FIG. 8A: Overview of the co-complex structure. FIG. 8B: The Fo-Fc omit map of the pY peptide (contour level=3σ). The phosphate-binding residues (R96$_L$, T33$_H$, H35$_H$, R95$_H$) are shown. The residues G55$_H$ and G56$_H$ from CDR-H2 form a shape-complementary conformation that accommodates the backbone structure of the pY-proceeding residue. FIG. 8C: same as 8B, except the three bound waters and their binding residues (Y91$_L$, N52$_H$, Y100$_H$) are shown.

FIG. 9A and FIG. 9B depict crystal structure of 4G10-S5$^{4D5}$/LpYL complex superimposed with the design model. FIG. 9A: The LpYL peptide shows a clear omit map (Fo-Fc, contour level=3σ) for all three residues. The serine at the position 95A$_L$ in the engineered CDR-L3 forms a new hydrogen bond to the existing bound water in the crystal structure. The residue T95$_L$ in the engineered CDR-L3 forms a hydrogen bond to S92$_L$. FIG. 9B: Overlay of the crystal structure and the computational modeling shows close agreement.

DETAILED DESCRIPTION OF THE INVENTION

Figures 1A, 1B, 1C:
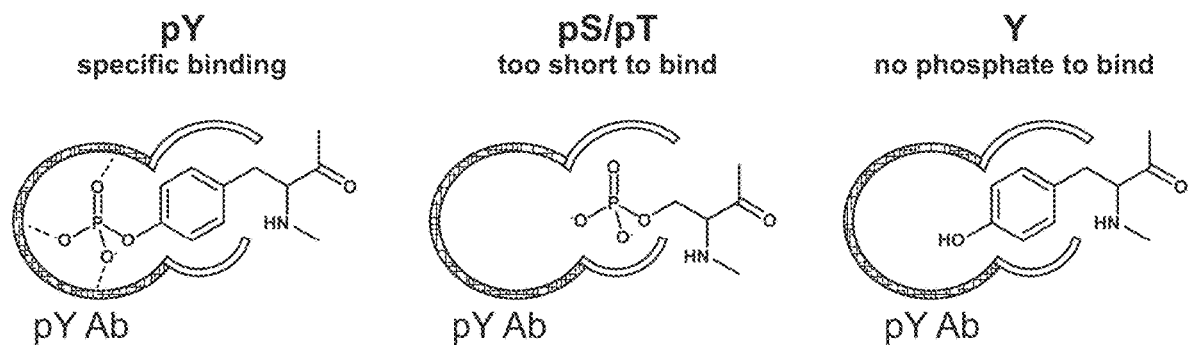
FIG. 1A is a schematic diagram depicting a phosphotyrosine in the binding pocket of a pY antibody.
FIG. 1B is a schematic diagram depicting a pS residue with the pY antibody binding pocket. The pS is too short to reach the phosphate group to the binding pocket.
FIG. 1C is a schematic diagram depicting a non-phosphorylated residue with the pY antibody, having no phosphate group to bind.
Figure 2:
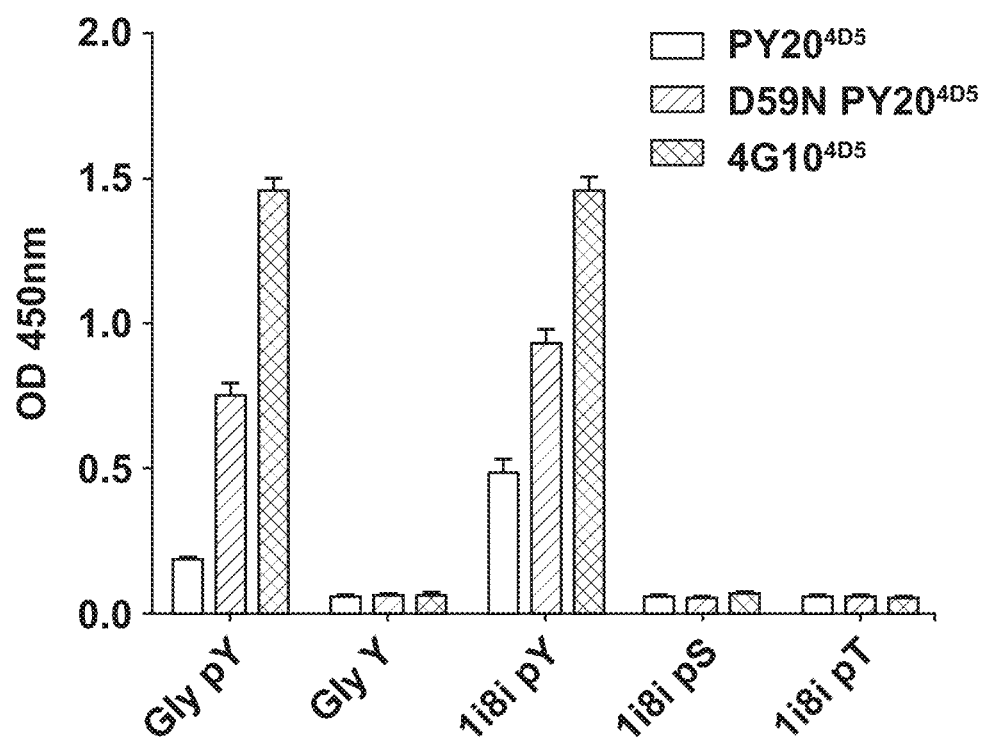
FIG. 2 depicts specificity measured by ELISA assay shows and affinity improvements. The bindings between the Fab phages (displaying PY20$^{4D5}$, D59N PY20$^{4D5}$, and 4G10$^{4D5}$) and the peptides containing different chemical groups (Y, pY, pS, and pT) were tested by ELISAs. All three Fabs show binding to pY peptides in a sequence-independent manner. No detectable binding was observed for pS, pT, and Y peptides. Gly pY: GGGpYGGG (SEQ ID NO: 87). GlyY: GGGYGGG (SEQ ID NO: 88). 1i8i pY: GEKKGNYVVTpYA (SEQ ID NO: 102). 1i8i pS: GEKKGNYVVTpSA (SEQ ID NO: 103). 1i8i pT: GEKKGNYVVTpTA (SEQ ID NO: 104).
Figure 5A:
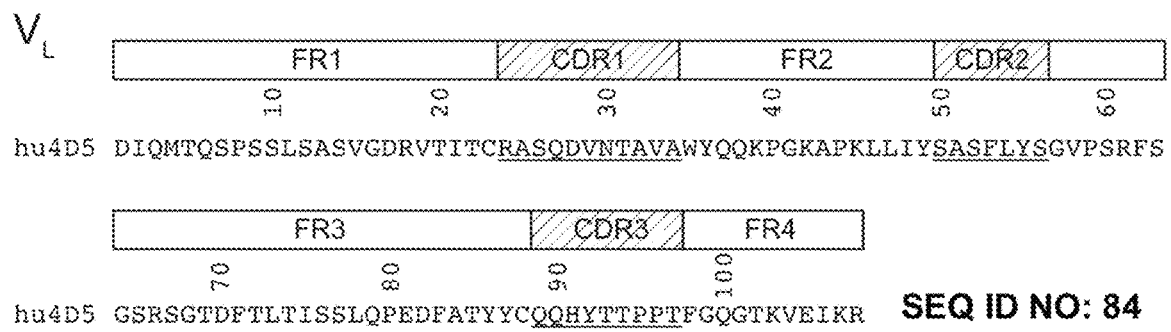
FIG. 5A: Map of 4D5 light chain variable region, showing framework and CDR sequences (underlined).
Figure 5B:
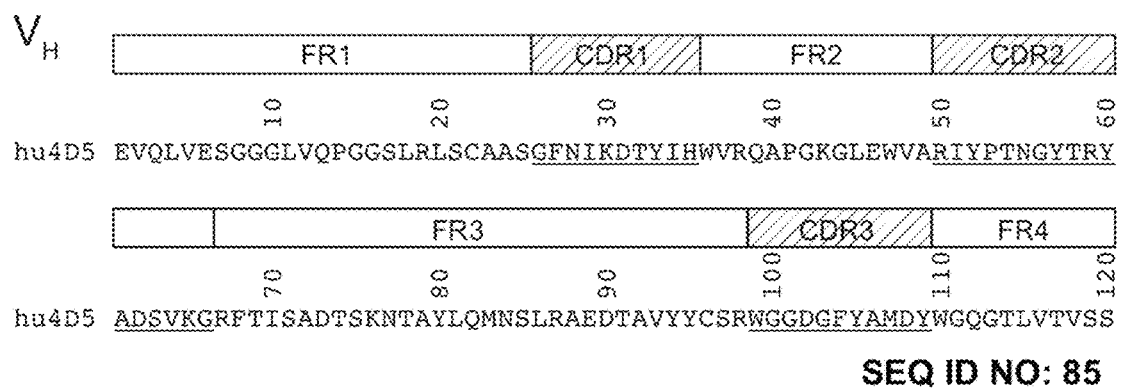
FIG. 5B: Map of 4D5 heavy chain variable region, showing framework and CDR sequences (underlined).
Figures 6A, 6B:
FIG. 6A and FIG. 6B depict sequence consensus of the top-12 hits from the CDR-L3 phage selection, showing strong sequence preferences. The top-12 hits showed two unique sequence motifs.
Figure 10:
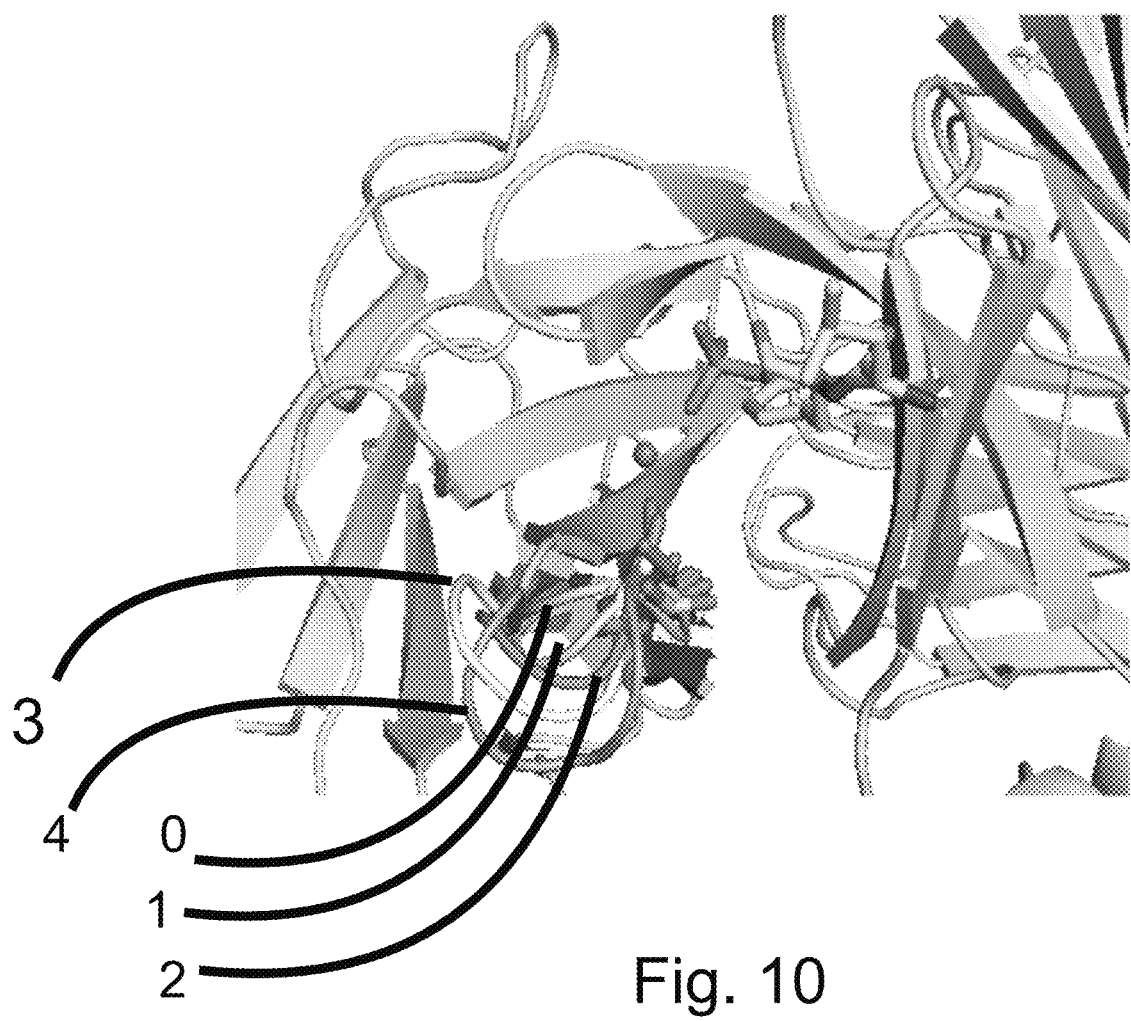
FIG. 10 depicts computational modeling of CDR-L3 insertions to create additional contacts to the pY group. Based on the 4G10$^{4D5}$/LpYL structure, different numbers of residues inserted in the CDR-L3 loop was modeled. Labels 0, 1, 2, 3, and 4 mark representative loops of the 0-, 1-, 2-, 3-, and 4-residue insertions, respectively. The last residue in the insertion is modeled as serine in this case. The orientation of serine gradually turns toward the crystal water that mediates a hydrogen bonds to the pY residue. The serine of the 3- or 4-residue insertion has a chance to create a hydrogen bond to the crystal water.

The invention encompasses novel pY antibodies and other compositions directed to the binding of phosphorylated tyrosines. The phosphotyrosines bound by the compositions of the invention may comprise phosphorylated tyrosine residues in a peptide or protein.

By the studies disclosed herein, the structural and physiochemical interactions of extant pY antibodies that impart pY binding affinity were determined. By these novel discoveries, engineered antibodies and other polypeptides with high affinity for phosphorylated tyrosine residues in proteins were designed. The improved sequences create a novel, additional binding interaction with phosphorylated tyrosine which improves the affinity of antibody binding and broadens the range of phosphotyrosine-containing proteins that may be effectively bound. The novel interaction may be a direct interaction with phosphotyrosine, or may comprise an indirect interaction, for example by a bridging water or other molecule.

The scope of the invention encompasses what will be referred to herein as a pY binding composition. The pY binding compositions of the invention may comprise any number of proteins, peptides, or other compositions of matter that bind pY residues of proteins with high affinity, such as antibodies, antibody fragments, and other compositions of matter.

The pY binding compositions of the invention comprise three elements:
  a scaffold body;
  pY complementarity-determining regions, comprising one or more of a CDR L1 sequence, a CDR L2 sequence, a CDR H1 sequence, a CDR H2 sequence, and a CDR-H3 sequence; and
  a novel engineered CDR L3 sequence which imparts enhanced affinity for phosphotyrosine.

Each element of the pY binding composition is described next.

The following description will recite or refer to various polypeptide sequences, such as antibody scaffold sequences and CDR sequences, including novel engineered CDRs. It will be understood that reference to such sequences is intended to encompass variants of such sequences. Variants, as used herein, includes variants of the enumerated sequences, such as amino acid substitutions, amino acid additions or deletions, truncations, subsequences and other variations of the enumerated sequence. In various embodiments, variants have at least 75%, at least 80%, at least 90%, at least 95%, or at least 99% sequence identity to the enumerated sequence.

SCAFFOLD BODY. The scaffold body comprises a composition that supports pY binding elements, specifically, complementarity-determining regions, including the novel engineered complementarity-determining sequences of the invention.

In a primary implementation, the scaffold body comprises an antibody or portion thereof In one embodiment, the pY binding composition of the invention comprises a whole, or substantially whole, antibody. In such implementations, the scaffold body, as referred to herein, will comprise all parts of a whole antibody except the complementarity-determining regions. As known in the art, a whole antibody comprises a dimer, each dimer comprising a heavy chain and a light chain. The heavy chain comprises three constant regions, $C_{H2}$ and $C_{H3}$, below the hinge, and $C_{H1}$ above the hinge. The heavy chain also comprises a variable region $V_H$ which comprises framework sequences that present the three heavy chain CDRs. The light chain comprises one constant region $C_L$, which is paired with $C_{H1}$, and a variable region $V_L$, comprising framework sequences which contain and present the three light chain CDRs.

In alternative implementations, the pY binding composition of the invention comprises an antibody fragment, for example, a Fab (Fragment, antigen binding), for example, an antibody fragment which retains phosphotyrosine binding ability. In such implementations, the scaffold body, as referred to herein, will comprise a subset of the parts of a whole antibody, depending on the particular fragment configuration of the composition. In one embodiment, the antibody fragment is a Fab (product of papain cleavage) or a Fab' (product of pepsin cleavage), comprising $C_H1$, $V_H$, $C_L$, and $C_L$ sequences and lacking the FC portion of the antibody. In one embodiment, the composition is a F(ab')2 fragment, comprising a Fab' dimer. In one embodiment, the pY binding composition of the invention comprises a single chain variable fragment (scFv), comprising a fusion protein of the VH and VL sequences of an antibody, wherein the chain sequences are joined by a linker sequence, for example, a linker of 10-50 amino acids, for example about 20-25 amino acids, for example, comprising glycine, serine, and/or threonine.

For example, in pY binding compositions comprising whole or substantially whole antibodies, the scaffold body may comprise the $C_H1$ segment, $C_H2$ segment, $C_H3$ segment, non-CDR segments of the $V_H$ segment, the $C_L$ segment, and the non-CDR segments of the $V_L$ segment of a selected antibody, or may comprise a hybrid derived from multiple antibody sequences, or may comprise a novel engineered sequence. In pY binding compositions comprising antibody fragments, the scaffold body may comprise the $C_H1$ segment, non-CDR segments of the $V_H$ segment, the $C_L$ segment, and the non-CDR segments of the $V_L$ segment of the selected antibody. In pY binding compositions comprising scFv's, the scaffold body may comprise non-CDR segments of the $V_H$ segment, and the non-CDR segments of the $V_L$ segment of the selected antibody, and a linker sequence, in some embodiments comprising 10-50 amino acids, for example about 20-25 amino acids, for example, comprising glycine, serine, and/or threonine.

Other scaffold body formats are within the scope of the invention as well, comprising any amino acid sequence that can orient and present the CDRs to achieve phosphotyrosine binding, include non-immunoglobulin protein scaffolds, synthetic antibody mimetics, and other compositions, as known in the art.

The scaffold body compositions of the invention may comprise any type of immunoglobulin. The antibodies or immunoglobulins of the invention may comprise any Ig isotype, for example, IgG, IgA, IgD, IgE and IgM forms. The IgG sequences may comprise any isoform, for example, IgG1, IgG2, IgG3 and IgG4 from human or other animal sources In certain embodiments of the invention, the scaffold body is derived from the sequences of the 4G10 antibody, as known in the art. The 4G10 antibody is described in U.S. Pat. No. 6,824,989, "Recombinant Monoclonal Antibody to Phosphotyrosine-Containing Proteins," by Eisinger et al. The 4G10 heavy and light chain sequences are listed herein as SEQ ID NO: 34 and SEQ ID NO: 35, respectively.

In certain embodiments of the invention, the scaffold body is derived from the sequences of the PY20 antibody, as known in the art. The Py20 antibody is described in Glenney et al., 1988, Monoclonal antibodies to phosphotyrosine, J Immunological Methods, 109: 277-285.

In certain embodiments of the invention, the scaffold body derived from the sequences of known pY antibodies, including, for example, Py2, 129, Py42, Py54, Py69, 2G8, P-Tyr-1000, and APY03, as known in the art. Numerous antibodies with specificity for specific phosphotyrosine compositions are also known in the art, for example, as reviewed in Mandell, 2003, Phosphorylation State-Specific Antibodies, American Journal of Pathology, Vol. 163, No. 5, November 2003.

In other implementations, the scaffold body comprises sequences of an established antibody platform for stable and efficient expression. In this implantation, CDRs imparting pY affinity are grafted onto a scaffold having good production properties, such as stable expression or high yields in expression systems. In one embodiment, the antibody scaffold is humanized antibody scaffold, wherein the scaffold has been engineered to provoke minimal immune response when administered to a human subject. The antibody scaffold may be selected from any number of established platforms for CDR grafting.

Exemplary scaffolds include the 4D5 scaffold, for example, as described in Carter et al., Humanization of an anti p185-HER2 antibody for human cancer therapy *Proc. Natl. Acad. Sci. USA* 1992, 89, 4285, also described in U.S. Pat. No. 6,870,034, Protein Purification, by Breece. The 45D heavy and light chain sequences are listed herein as SEQ ID NO: 36 and SEQ ID NO: 37, respectively.

Additional scaffolds for CDR grafting or affinity transfer include those described in: United States Patent Application Publication Number 2016/0003843, Engineered Antibody Scaffolds, by Wells et al; Fab1H, Fab12E, FabC12 scaffolds described in Baily et al., Locking the Elbow: Improved Antibody Fab Fragments as Chaperones for Structure Determination, J Mol. Biol. 2018 430:337-347; sc60 scaffold as described in Koerber et al., An Improved Single-chain Fab Platform for Efficient Display and Recombinant Expression, J Mol. Boil. 2015, 427: 576-586; and the Fab A33 scaffold, as described in Cobina et al., Insights into the stability of a therapeutic antibody Fab fragment by molecular dynamics and its stabilization by computational design, 2019 doi/10.1101/644369 bioRxiv.

CDR Regions. The pY binding compositions of the invention will comprise one or more CDR regions which impart pY binding affinity. Each CDR comprises a peptide loop extending from the antibody variable region, which may work independently or, more commonly, in concert with other CDR sequences, including CDR sequences on the complementary heavy or light chain, to impart specificity and binding of the target moiety. Each CDR is flanked by a framework sequence of the corresponding light or heavy chain, which frameworks aid in the orientation of the CDR sequences and presentation of the CDR loops.

In a primary embodiment, the pY binding compositions of the invention will comprise a CDR L1 sequence, a CDR L2, CDR H1 sequence, a CDR H2 sequence, and a CDR H3 sequence. In alternative implementations, one or more of the CDR L1, CDR L2, CDR H1, CDR H2, and CDR H3 sequences is omitted.

The CDR sequences of the pY binding composition of the invention may be selected to impart specificity for and phosphotyrosine target. In a primary implementation, the CDR sequences of the pY binding composition are selected to impart pan-pY specificity, meaning specificity for phosphorylated tyrosine residues in a large number of proteins, e.g. broadly binding to pY residues in a way that is wholly or substantially independent of the surrounding amino acid sequences, secondary or tertiary structures, etc of the target protein. Pan-specificity is desirable for broad use across any number of diverse phosphopeptide targets.

In an alternative embodiment, the pY binding composition of the invention comprises a composition having specificity for one, or a small number of, phosphorylated proteins, wherein the specificity is sequence specific and limited to, or optimized for, pY residues in a specific sequence, structure, or context.

In a primary embodiment, the CDRs of the pY binding composition are selected from the 4G10 antibody, as set forth in Table 1. In one embodiment, the selected CDR L1, CDR L2, CDR H1, CDR H2, and CDR H3 sequences are 4G10 CDR L1 (SEQ ID NO: 24), CDR L2 (SEQ ID NO: 25), CDR H1 (SEQ ID NO: 26), CDR H2 (SEQ ID NO: 27) and CDR H3 (SEQ ID NO: 28). In alternative embodiments, the selected CDRs comprise a subset of 4G10 CDR L1, CDR L2, CDR H1, CDR H2, and CDR H3 sequences, comprising one or more of 4G10 CDR L1 (SEQ ID NO: 24), CDR L2 (SEQ ID NO: 25), CDR H1 (SEQ ID NO: 26), CDR H2 (SEQ ID NO: 27) and CDR H3 (SEQ ID NO: 28).

TABLE 1

4G10 light and heavy CDR sequences.

| 4G10 Variable Region | Sequence ID NO | Sequence |
|---|---|---|
| Light Chain CDR 1 (L1) | SEQ ID NO: 24 | RASSSVSSSYLH |
| Light Chain CDR 2 (L2) | SEQ ID NO: 25 | STSNLAS |
| Heavy Chain CDR 1 (H1) | SEQ ID NO: 26 | YTFTENTV |
| Heavy Chain CDR 2 (H2) | SEQ ID NO: 27 | IGGINPYYGGSIFSPKF |
| Heavy Chain CDR 3 (H3) | SEQ ID NO: 28 | RAGAYYF |

In another embodiment, the CDRs of the pY binding composition are selected from the PY20 antibody, as set forth in Table 2. In one embodiment, the selected CDR L1, CDR L2, CDR H1, CDR H2, and CDR H3 sequences are PY20 CDR L1 (SEQ ID NO: 29), PY20 CDR L2 (SEQ ID NO: 30), PY20 CDR H1 (SEQ ID NO: 31), PY20 CDR H2 (SEQ ID NO: 32) and PY20 CDR H3 (SEQ ID NO: 33). In alternative embodiments, the selected CDRs comprise a subset of PY20 CDR L1, CDR L2, CDR H1, CDR H2, and CDR H3 sequences, comprising one or more of PY20 CDR L1 (SEQ ID NO: 29), CDR L2 (SEQ ID NO: 30), CDR H1 (SEQ ID NO: 31), CDR H2 (SEQ ID NO: 32) and CDR H3 (SEQ ID NO: 33).

TABLE 2

PY20 light and heavy CDR sequences.

| 4G10 Variable Region | Sequence ID NO | Sequence |
|---|---|---|
| Light Chain CDR 1 (L1) | SEQ ID NO: 29 | SASQGISNYLN |
| Light Chain CDR 2 (L2) | SEQ ID NO: 30 | YTSSLHS |
| Heavy Chain CDR 1 (H1) | SEQ ID NO: 31 | YTFTEYTM |
| Heavy Chain CDR 2 (H2) | SEQ ID NO: 32 | MGGINPNSGGTRDNQRF |
| Heavy Chain CDR 3 (H3) | SEQ ID NO: 33 | RGPYGNYYNSYYF |

In other embodiments, the CDRs of the pY binding composition are selected from the pY antibodies known in the art, for example, Py2, 129, Py42, Py54, Py69, 2G8, P-Tyr-1000, and APY03, as known in the art.

In one embodiment, the selected CDR L1, CDR L2, CDR H1, CDR H2, and CDR H3 sequences are derived from a single pY antibody type. In an alternative implementation, hybrid compositions are made selecting CDR L1, CDR L2, CDR H1, CDR H2, and CDR H3 sequences derived from two or more antibody types.

Engineered CDR L3 Sequences. The pY binding compositions of the invention comprise novel CDR L3 sequences that facilitate improved binding over prior art pY binders. Without being bound to any specific theory, it is believed that the novel lengthened CDR-L3 loop sequences of the invention improve binding to phosphorylated tyrosine residues by creating additional interactions to the pY group from its solvent-exposed side, for example, creating an additional hydrogen bond to the water molecules mediating the phosphate binding. In one aspect, the scope of the invention is directed to a polypeptide sequence comprising an improved CDR L3.

The novel CDR L3 sequences of the invention comprise lengthened sequences of the 4G10 CDR L3, which comprises YSGYR (SEQ ID NO: 5). In the improved variants of the invention, the G residue is substituted with insertions that lengthen the chain and that enhance binding to phosphotyrosine (pY). In one embodiment, the insertion is a sequence of any length greater than 2 amino acids. In some embodiments, the inserted sequence may comprise 2, 3, 4, 5, 6, 7, 8, 9, 10 or more amino acids. In one embodiment, the inserted sequence is any polypeptide sequence of four amino acids in length. In one embodiment, the modified 4G10 L3 CDR sequence of the invention comprises SEQ ID NO: 1, wherein the inserted sequence between samino acids 2 and 3 may comprise 2, 3, 4, 5, 6, 7, 8, 9, or 10 amino acids of any composition. In one embodiment, the insertion is any polypeptide sequence of four amino acids in length, being any amino acids of any composition.

In one embodiment, the engineered CDR L3 comprises SEQ ID NO: 2: $X_1X_2TS$, wherein $X_1$ and $X_2$ may comprise any amino acid. In one embodiment, $X_1$ is selected from arginine, proline, and serine. In one embodiment, $X_2$ is selected from arginine, histidine, leucine, serine, and tryptophan.

In one embodiment, the engineered CDR L3 comprises SEQ ID NO: 3: $X_1X_2SS$, wherein $X_1$ and $X_2$ may comprise any amino acid. In one embodiment, $X_1$ is selected from arginine, alanine, glycine, and serine. In one embodiment, $X_2$ is selected from arginine, proline, glycine, and tyrosine.

In one embodiment, the engineered CDR L3 comprises SEQ ID NO: 4: $X_1X_2X_3G$, wherein $X_1$, $X_2$, and $X_3$ may comprise any amino acid. In one embodiment, $X_1$ is selected from arginine, alanine, glycine, and serine. In one embodiment, $X_2$ is selected from arginine, proline, glycine, and tyrosine. In one embodiment, $X_3$ is selected from lysine, tyrosine, methionine, and tryptophan.

In various embodiments, the CDR L3 sequence comprises a sequence selected from SEQ ID NO: 6-SEQ ID NO: 23, as listed in Table 3 below.

TABLE 3

Engineered CDR L3 sequences of the invention

| SEQ ID NO: 5 Original 4G10 CDR L3 sequence | YSGYR |
|---|---|
| SEQ ID NO: 6 | YSPWTSYR |
| SEQ ID NO: 7 | YSRHTSYR |
| SEQ ID NO: 8 | YSRSSSYR |
| SEQ ID NO: 9 | YSRLTSYR |
| SEQ ID NO: 10 | YSRRTSYR |
| SEQ ID NO: 11 | YSSRTSYR |
| SEQ ID NO: 12 | YSSRKGYR |
| SEQ ID NO: 13 | YSAGMGYR |
| SEQ ID NO: 14 | YSGRYGYR |
| SEQ ID NO: 15 | YSRPYGYR |

TABLE 3-continued

Engineered CDR L3 sequences of the invention

| | |
|---|---|
| SEQ ID NO: 5 Original 4G10 CDR L3 sequence | YSGYR |
| SEQ ID NO: 16 | YSRYKGYR |
| SEQ ID NO: 17 | YSRPWGYR |
| SEQ ID NO: 18 | YSSRKGYR |
| SEQ ID NO: 19 | YSGRYGYR |
| SEQ ID NO: 20 | YSRPYGYR |
| SEQ ID NO: 21 | YSRYKGYR |
| SEQ ID NO: 22 | YSRPWGYR |
| SEQ ID NO: 23 | YSRRTSYR |

The performance of various CDR L3 sequences was tested, as set forth in Table 4.

TABLE 4

Kinetic measurements of antibody/pY binding using biolayer interferometry. Antibodies used in this study were tested for their binding kinetics to a pY peptide (GGGpYGGG).

| Name | L3 sequence* | $k_{on}$ (1/Msec) | $k_{off}$ (1/sec) | $K_D$ (M) |
|---|---|---|---|---|
| PY20$^{4D5}$ | n/a | $1.09 \times 10^5 \pm 6.35 \times 10^3$ | $2.00 \times 10^{-1} \pm 1.56 \times 10^{-3}$ | $1.83 \times 10^{-6} \pm 1.08 \times 10^{-7}$ |
| D59N PY20$^{4D5}$ | n/a | $1.19 \times 10^5 \pm 4.61 \times 10^3$ | $1.21 \times 10^{-1} \pm 1.16 \times 10^{-3}$ | $1.02 \times 10^{-6} \pm 4.09 \times 10^{-8}$ |
| 4G10$^{4D5}$ | G | $8.22 \times 10^4 \pm 2.13 \times 10^3$ | $2.28 \times 10^{-2} \pm 9.53 \times 10^{-5}$ | $2.77 \times 10^{-7} \pm 7.27 \times 10^{-9}$ |
| 4G10-S1$^{4D5}$ | PWTS (SEQ ID NO: 90) | $1.41 \times 10^5 \pm 1.75 \times 10^3$ | $7.89 \times 10^{-3} \pm 4.89 \times 10^{-5}$ | $5.59 \times 10^{-8} \pm 7.75 \times 10^{-10}$ |
| 4G10-S2$^{4D5}$ | RHTS (SEQ ID NO: 91) | $1.33 \times 10^5 \pm 1.94 \times 10^3$ | $6.90 \times 10^{-3} \pm 4.73 \times 10^{-5}$ | $5.19 \times 10^{-8} \pm 8.36 \times 10^{-10}$ |
| 4G10-S3$^{4D5}$ | RSSS (SEQ ID NO: 92) | $1.34 \times 10^5 \pm 1.39 \times 10^3$ | $8.76 \times 10^{-3} \pm 4.89 \times 10^{-5}$ | $6.56 \times 10^{-8} \pm 7.72 \times 10^{-10}$ |
| 4G10-S4$^{4D5}$ | RLTS (SEQ ID NO: 93) | $1.51 \times 10^5 \pm 2.00 \times 10^3$ | $7.20 \times 10^{-3} \pm 4.65 \times 10^{-5}$ | $4.77 \times 10^{-8} \pm 7.03 \times 10^{-10}$ |
| 4G10-S5$^{4D5}$ | RRTS (SEQ ID NO: 94) | $7.72 \times 10^4 \pm 1.36 \times 10^3$ | $4.41 \times 10^{-3} \pm 2.60 \times 10^{-5}$ | $5.72 \times 10^{-8} \pm 1.07 \times 10^{-9}$ |
| 4G10-S6$^{4D5}$ | SRTS (SEQ ID NO: 95) | $1.36 \times 10^5 \pm 1.96 \times 10^3$ | $7.47 \times 10^{-3} \pm 4.49 \times 10^{-5}$ | $5.48 \times 10^{-8} \pm 8.56 \times 10^{-10}$ |
| 4G10-G1$^{4D5}$ | SRKG (SEQ ID NO: 96) | $1.09 \times 10^5 \pm 1.19 \times 10^3$ | $6.63 \times 10^{-3} \pm 3.43 \times 10^{-5}$ | $6.11 \times 10^{-8} \pm 7.38 \times 10^{-10}$ |
| 4G10-G2$^{4D5}$ | AGMG (SEQ ID NO: 97) | $1.74 \times 10^5 \pm 1.89 \times 10^3$ | $9.97 \times 10^{-3} \pm 6.05 \times 10^{-5}$ | $5.75 \times 10^{-8} \pm 7.15 \times 10^{-10}$ |
| 4G10-G3$^{4D5}$ | GRYG (SEQ ID NO: 98) | $1.34 \times 10^5 \pm 1.32 \times 10^3$ | $6.16 \times 10^{-3} \pm 3.33 \times 10^{-5}$ | $4.60 \times 10^{-8} \pm 5.18 \times 10^{-10}$ |
| 4G10-G4$^{4D5}$ | RPYG (SEQ ID NO: 99) | $1.68 \times 10^5 \pm 1.69 \times 10^3$ | $6.07 \times 10^{-3} \pm 3.65 \times 10^{-5}$ | $3.61 \times 10^{-8} \pm 4.23 \times 10^{-10}$ |
| 4G10-G5$^{4D5}$ | RYKG (SEQ ID NO: 100) | $1.22 \times 10^5 \pm 1.65 \times 10^3$ | $5.33 \times 10^{-3} \pm 3.42 \times 10^{-5}$ | $4.37 \times 10^{-8} \pm 6.53 \times 10^{-10}$ |
| 4G10-G6$^{4D5}$ | RPWG (SEQ ID NO: 101) | $1.76 \times 10^5 \pm 1.88 \times 10^3$ | $5.54 \times 10^{-3} \pm 3.46 \times 10^{-5}$ | $3.14 \times 10^{-8} \pm 3.89 \times 10^{-10}$ |

*For 4G10$^{4D5}$ and its variants, the 93$_L$ position (defined by 4G10$^{4D5}$) and its replacement sequences (between 92$_L$ and 94$_L$) are shown, respectively. The 93$_L$ position defined by 4G10$^{4D5}$ is not applicable to PY20$^{4D5}$ and D59N PY20$^{4D5}$ because their CDR-L3 is one-residue lengthier than 4G10$^{4D5}$. The sequence motifs XX(T/S)S and XXXG are shown in bold.

Improved pY Antibodies and Compositions Based Thereon.

The compositions of the invention encompass improved and engineered antibodies, fragments thereof, or other compositions for high affinity binding of pY.

In a first aspect, the pY binding compositions of the invention may comprise an improved pY antibody or antibody fragment. In this implementation, existing pY antibodies and/or their antigen binding fragments are improved by the inclusion of the engineered L3 CDR of the invention, i.e. being improved pY antibodies and fragments thereof wherein the original CDR L3 of the antibody is replaced with a CDR L3 sequence of the invention. In this implementation, the body scaffold and CDR L1, CDR L2, CDR H1, CDR H2, and CDR H3 sequences may be those of a selected pY antibody and the composition further comprises an engineered CDR L3 sequence of the invention, wherein the engineered CDR L3 comprises a sequence selected from the group consisting of: SEQ ID NO: 1-SEQ ID NO: 4 and SEQ ID NO: 6-SEQ ID NO: 23.

In one embodiment, the CDR L3 sequence comprises SEQ ID NO: 15 (denoted G4). In one embodiment, the CDR L3 sequence comprises SEQ ID NO: 22 (denoted G6). In one embodiment, the CDR L3 sequence comprises SEQ ID NO: 10 (denoted S5). In one embodiment, the CDR L3 sequence comprises SEQ ID NO: 12 (denoted G1). In one embodiment, the L3 sequence comprises SEQ ID NO: 14 (denoted G3).

In various embodiments, the pY binding composition of the invention comprises:

an antibody or antibody fragment, comprising:
    a body scaffold comprising sequences of one or more selected antibodies;
    a CDR L1 sequence, a CDR L2 sequence, a CDR H1 sequence, a CDR H2 sequence, and a CDR H3 sequence, wherein one or more of the CDR sequences impart affinity for pY; and
    a CDR L3 sequence comprising a sequence selected from the group consisting of: SEQ ID NO: 1-SEQ ID NO: 4 and SEQ ID NO: 6-SEQ ID NO: 23.

In various embodiments, the pY binding composition is a whole antibody, or a fragment thereof, for example, a Fab, a Fab', a F(ab)$_2$, or a scFV, for example, wherein the fragment retains phosphotyrosine binding ability.

In one embodiment, the body scaffold comprises heavy and light chain sequences of the 4G10 antibody. In one embodiment, the body scaffold comprises heavy and light chain sequences of the 4D5 antibody.

In one embodiment, the CDR L1, CDR L2, CDR H1, CDR H2 and CDR H3 sequences which impart affinity for pY comprise one or more of 4G10 CDR L1 (SEQ ID NO: 24), 4G10 CDR L2 (SEQ ID NO: 25), 4G10 CDR H1 (SEQ ID NO: 26), 4G10 CDR H2 (SEQ ID NO: 27) and 4G10 CDR H3 (SEQ ID NO: 28).

In one embodiment, the CDR L1, CDR L2, CDR H1, CDR H2 and CDR H3 sequences which impart affinity for pY comprise one or more of PY20 CDR L1 (SEQ ID NO: 29), PY20 CDR L2 (SEQ ID NO: 30), PY20 CDR H1 (SEQ ID NO: 31), PY20 CDR H2 (SEQ ID NO: 32) and PY20 CDR H3 (SEQ ID NO: 33).

In various embodiments, the CDR L1, CDR L2, CDR H1, CDR H2 and CDR H3 sequences which impart affinity for pY may comprise CDRs selected from one or more of from Py2, 129, Py42, Py54, Py69, 2G8, P-Tyr-1000, and APY03 antibodies.

In one implementation, the scope of the invention encompasses an improved 4G10 antibody, or fragment thereof, wherein the 4G10 CDR L3 sequence is replaced with an engineered CDR L3 sequence of the invention. In this implementation, the pY binding composition comprises: a scaffold body comprising 4G10 sequences; 4G10 CDRs: L1 (SEQ ID NO: 24), L2 (SEQ ID NO: 25), H1 (SEQ ID NO: 26), H2 (SEQ ID NO: 27) and H3 (SEQ ID NO: 28) CDRs; and an engineered L3 sequence comprising a sequence selected from the group consisting of: SEQ ID NO: 1-SEQ ID NO: 4 and SEQ ID NO: 6-SEQ ID NO: 23 (wherein the original 4G10 CDR L3 is replaced). In one embodiment, the CDR L3 sequence comprises SEQ ID NO: 15 (G4). In one embodiment, the L3 sequence comprises SEQ ID NO: 22 (G6). In one embodiment, the L3 sequence comprises SEQ ID NO: 10 (S5). In one embodiment, the L3 sequence comprises SEQ ID NO: 12 (G1). In one embodiment, the L3 sequence comprises SEQ ID NO: 14 (G3). The scope of the invention encompasses variants of the foregoing improved 4G10 antibodies and fragments thereof, including variants having at least 95% sequence identity to enumerated sequences.

In one embodiment, the pY binding composition of the invention comprises an improved 4G10 antibody, or a fragment thereof, wherein the improved 4G10 antibody comprises: a light chain comprising SEQ ID NO: 35, wherein non-consecutive residues 91 and 92 are separated by a grafted CDR-L3 sequence comprising a sequence selected from the group consisting of SEQ ID NO: 1-SEQ ID NO: 4 and SEQ ID NO: 6-SEQ ID NO: 23; and a heavy chain comprising SEQ ID NO: 34. The scope of the invention encompasses variants of the foregoing improved 4G10 antibodies and fragments thereof, including variants having at least 95% sequence identity to enumerated sequences.

In one embodiment, the pY binding composition of the invention comprises an improved 4G10 antibody, or a fragment or variant of such antibody, wherein the improved 4G10 antibody comprises: a light chain comprising SEQ ID NO: 36, comprising a grafted G4 CDR L3 sequence; and a heavy chain comprising SEQ ID NO: 34. The scope of the invention encompasses variants of the foregoing improved 4G10 antibodies and fragments thereof, including variants having at least 95% sequence identity to enumerated sequences.

In one embodiment, the pY binding composition of the invention comprises an improved 4G10 antibody, or a fragment of variant of such antibody, wherein the improved 4G10 antibody comprises: a light chain comprising SEQ ID NO: 37, comprising a grafted G6 CDR-L3 sequence; and a heavy chain comprising SEQ ID NO: 34. The scope of the invention encompasses variants of the foregoing improved 4G10 antibodies and fragments thereof, including variants having at least 95% sequence identity to enumerated sequences.

In another embodiment, the pY binding composition of the invention comprises a body scaffold, for example comprising heavy and light chain sequences of a selected antibody other than 4G10, wherein the CDR L1, CDR L2, CDR H1, CDR H2, and CDR H3 sequences of 4G10 are grafted onto the body scaffold; and further comprising an engineered CDR L3 sequence of the invention (i.e., wherein the grafted CDRs replace the original CDRs of the antibody). This implementation represents affinity transfer of the improved 4G10 antibody described herein to another antibody platform, for example, a humanized antibody, an antibody having high thermostability, or an antibody having high expression capacity. For example, in one embodiment, the scope of the invention encompasses an antibody, or fragment thereof, comprising: a grafted CDR L1 comprising SEQ ID NO: 29; a grafted CDR L2 comprising SEQ ID NO: 30; a grafted CDR H1 comprising SEQ ID NO: 31; a grafted CDR H2 comprising SEQ ID NO: 32; a grafted CDR H3 comprising SEQ ID NO: 33; and a grafted CDR L3 comprising a sequence selected from the group consisting of SEQ ID NO: 1-SEQ ID NO: 4 and SEQ ID NO: 6-SEQ ID NO: 23. In one embodiment, the grafted CDR L3 comprises SEQ ID NO: 15 (G4). In one embodiment, the grafted CDR L3 comprises SEQ ID NO: 22 (G6). The scope of the invention encompasses variants of the foregoing antibodies comprising affinity transfer from improved 4G10 antibodies and fragments thereof, including variants having at least 95% sequence identity to enumerated sequences.

In one embodiment, the pY binding composition of the invention comprises a body scaffold comprising 4D5 heavy and light chain sequences, wherein the CDR L1, CDR L2, CDR H1, CDR H2, and CDR H3 sequences of 4G10 are grafted onto the 45D body scaffold (replacing the original 4D5 CDRs); and further comprising an engineered CDR L3 sequence of the invention (replacing the original 4D5 CDR L3). This implementation represents affinity transfer of the improved 4G10 antibodies described herein to the 4D5 platform. In one embodiment, framework sequences of 4G10 are grafted into the antigen binding region of the 45D antibody. In one embodiment, the 45D framework sequences are retained. For example, in one embodiment, the pY binding composition of the invention comprises an antibody or fragment thereof, comprising: a light chain comprising SEQ ID NO: 39, wherein a CDR L3 sequence is grafted between non-consecutive residues 91 and 92 and wherein the CDR L3 sequence comprises a sequence selected from the group consisting of SEQ ID NO: 1-SEQ ID NO: 4 and SEQ ID NO: 6-SEQ ID NO: 23; and a heavy chain comprising SEQ ID NO: 43. The scope of the invention encompasses variants of the foregoing 4G10-4D5 antibodies and fragments thereof, including variants having at least 95% sequence identity to enumerated sequences.

In one embodiment, the pY binding composition of the invention comprises an antibody, or a fragment or variant thereof, wherein the antibody comprises a 4D5 antibody wherein CDR L1, CDR L2, CDR H1, CDR H2, and CDR H3 sequences from 4G10 are grafted thereon and further comprising a grafted G4 CDR L3 sequence. In one embodiment, such antibody comprises: a light chain comprising SEQ ID NO: 40; and a heavy chain comprising SEQ ID NO: 43. The scope of the invention encompasses variants of the foregoing antibody and fragments thereof, including variants having at least 95% sequence identity to enumerated sequences.

In one embodiment, the pY binding composition of the invention comprises an antibody, or a fragment or variant thereof, wherein the antibody comprises a 4D5 antibody wherein CDR L1, CDR L2, CDR H1, CDR H2, and CDR H3 sequences from 4G10 are grafted thereon and further comprising a grafted G6 CDRL3 sequence. In one embodiment, such antibody comprises: a light chain comprising SEQ ID NO: 41; and a heavy chain comprising SEQ ID NO: 43. The scope of the invention encompasses variants of the foregoing antibody and fragments thereof, including variants having at least 95% sequence identity to enumerated sequences.

In a related implementation, the 4D5 antibody is used as a body scaffold for pY binding compositions comprising the engineered CDR L3 sequences of the invention. In one implementation the pY binding composition of the invention comprises an antibody, or a fragment thereof, wherein the antibody comprises a 4D5 antibody wherein CDR sequences imparting pY specificity are grafted therein, including engineered CDR L3 sequences of the invention. In one embodiment, such antibody comprises: a light chain comprising SEQ ID NO: 38, wherein a CDR L1 is grafted between non-consecutive residues 23 and 24, a CDR L2 sequence is grafted between non-consecutive residues 38 and 39, and a CDR L3 sequence is grafted between non-consecutive residues 72 and 73, wherein the CDR L3 sequence comprises a sequence selected from the group consisting of SEQ ID NO: 1-SEQ ID NO: 4 and SEQ ID NO: 6-SEQ ID NO: 23; and a heavy chain comprising SEQ ID NO: 42, wherein a CDR H1 sequences is grafted between non-consecutive residues 26 and 27, a grafted CDR H2 sequence is grafted between non-consecutive residues 39 and 40, and a CDR H3 sequence is grafted between non-consecutive residues 73 and 74; wherein the grafted CDR sequences impart pY binding affinity. The CDR L1, CDR L2, CDR H1, CDR H2, and CDR H3 sequences may be selected from one or more pY binding antibodies, for example, Py2, pY20, 129, Py42, Py54, Py69, 2G8, P-Tyr-1000, and APY03 The scope of the invention encompasses variants of the foregoing engineered antibodies and fragments thereof, including variants having at least 95% sequence identity to enumerated sequences.

Functionalizations. The pY binding compositions of the invention may comprise any number of functional moieties. In one embodiment, functional molecules may be incorporated into the antibody, fragment thereof, or other compositions of the invention as fusion products, for example, being present at the C-terminus or N-terminus of heavy and/or light chains.

In one implementation, functionalization is be achieved by engineering light or heavy chain sequences of the pY binding compositions to express affinity tags, for example, at the C-terminus or N-terminus of heavy and/or light chains, wherein functional moieties bearing complementary affinity tags are joined to the affinity tag of the pY binding polypeptide by reacting under suitable conditions for conjugation. Exemplary affinity tags include, for example one member of a SpyCatcher-SpyTag system, SnoopCatcher-SnoopTag system, DogTag tagging system; Isopeptag tagging system; SdyTag tagging system; biotin-avidin tagging systems; strepavidin-biotin tagging systems; or polyhistidine tagging systems, e.g. 6-histidine HisTags, as known in the art.

Alternatively, functionalization may be achieved by chemical modification of solvent accessible residues in in the pY binding composition which can act as reactive handles, for example, residues in the constant region of the light or heavy chain. In one implementation, labels can be linked to the amino groups ($NH_2$ groups) of antibodies, including lysine amino groups or the N-terminal amino groups of the heavy and/or light chains. For example, functionalization can be achieved by incubating with an active ester derivative of a fluorophore, enzyme, or other functional molecule. In another implementation, amino acids with an SH group (cysteine and methionine) are functionalized, for example, cysteine groups in the hinge region. Antibodies are treated with 2-mercaptoethanol (2-ME), which cleaves the molecule at the hinge region, followed by reaction with a maleimide-activated fluorophore, enzyme, or other functional moiety Other exemplary residues for functionalization include solvent-accessible carboxyl groups of glutamic or aspartic acid residues. Other residues for functionalization include solvent accessible free amines of lysine residues, for example, stable amide linkages to functional moieties may be formed at such sites utilizing N-hydroxysuccinimide (NHS) esters, isothiocyanates, isocyanates, or acyl azides, as known in the art). In other implementations, functionalization is achieved by conjugation of functional moieties to solvent-accessible tyrosine residues. For example, conjugation to tyrosine may be achieved by the use of diazonium groups. Diazonium may additionally be utilized in the modification of lysine or histidine residues. Modification of solvent accessible N-terminal amines may be utilized for functionalization. For example, N-terminal transamination/oxime chemistries may be utilized to functionalize pY binding compositions. In other implementations, functional molecules are chemically conjugated to methionine or cysteine residues in the pY binding composition.

Functional moieties may comprise fluorescent labels, such as fluorescent proteins, fluorescent dyes, or fluorophores. Exemplary fluorescent labels include Fluorescein isothiocyanate, fluorescin, FITC, PE, PerCP, Rhodamine, aminomethylcoumarin, R-phycoerythrin, and fluorochrome dyes, as known in the art. Exemplary fluorescent dyes include ALEXA FLUOR™ (Invitrogen) dyes.

Functional moieties may comprise enzymes for detection and quantification assays, exemplary enzymes including for example, horseradish peroxidase, alkaline phosphatase, urease, and other enzymatic detection systems known in the art.

Other functional moities include affinity tags, epitope tags for binding of secondary labeled antibodies, and other moieties such as agents used in immunofluorescent methods, immunostaining, flow cytometry, and other methods. In therapeutic applications, the functional moiety may be a drug or other therapeutic agent.

pY binding compositions, such as antibodies or antibody fragments may be selected to have, or engineered to have, epitopes for binding by secondary antibodies. For example, the pY binding compositions of the invention may comprise epitopes for binding of secondary antibodies functionalized with fluorescent molecules, enzymes, or other moieties. In one embodiments, epitopes for secondary antibodies may be present in the Fc region of the light and/or heavy chain.

Nucleic Acids, Engineered Cells. In another aspect, the scope of the invention further encompasses nucleic acid constructs which code for the pY binding compositions of the invention. The nucleic acids may comprise expression vectors, plasmids, and/or genomes of cells engineered to express the polypeptides of the invention. The nucleic acid constructs of the invention may be coded utilizing codons optimized for expression in any host, including humans or other organisms such as yeast, insect cells, Cho cells, other rodent cells, bacterial cells and others.

In various embodiments, the nucleic acid constructs of the invention comprise nucleic acid sequences which code for a polypeptide, for example, the variable region of an antibody light chain, wherein the polypeptide comprises a CDR L3 comprising a sequence selected from the group consisting of SEQ ID NO: 1-SEQ ID NO: 4 and SEQ ID NO: 6-SEQ ID NO: 23. In various embodiments, the nucleic acid constructs of the invention code for antibodies, antibody fragments and other compositions disclosed herein, including SEQ ID NO: 1-SEQ ID NO: 43, and variants thereof, for example, sequences comprising at least 95% sequence identity.

In one embodiment, the scope of the invention encompasses cells transformed with a nucleic acid construct of the invention such that the cell will express a pY binding composition of the invention. In one embodiment, the transformed cells comprise human cells. In one embodiment, the transformed cells comprise rodent (e.g. mouse, rat, rabbit, CHO cells, etc.) cells. In one embodiment, the transformed cells comprise yeast, bacterial, insect, or other cells utilized as expression vectors. In one embodiment, the transformed cells comprise hybridomas.

Production of pY Binding Compositions. The pY binding compositions of the invention may be made by methods known in the art for the production of antibodies and antibody fragments. For example, recombinant antibody production methods may be utilized, wherein nucleic sequences are manipulated to express the compositions of the invention. Heavy and light chains can be produced in vitro and processed under suitable conditions to create antibodies (for example in the presence of reducing agents to form disulfide bonds), Fabs, Fab's, F(ab)2 products, by means known in the art. scFv products may be produced as fusion proteins. Polypeptides of the invention may be produced in cells of any type, including for example, yeast, bacterial, mouse, rat, rabbit, or CHO cells. Polypeptides of the invention may be produced in hybridomas. Exemplary platforms for heavy and light chain sequence manipulation and expression include those described in Gupta and Shukla, Microbial platform technology for recombinant antibody fragment production: A review, 2017 Critical Reviews in Microbiology, 43: 31-42; Birch and Racher, Antibody Production, 2006, Advanced Drug Delivery Reviews 58 (2006) 671-685; and Kunnert and Rinehart, Advances in Recombinant Antibody Production, 2016, Applied Microbiology and Biotechnology, 2016 100:3451-3461.

Methods of Use. The pY binding composition of the invention have affinity for phosphotyrosines. The engineered polypeptides of the invention may be utilized in any application. In one implementation, the pY binding compositions of the invention are configured as detection agents, for example, pY binding compositions comprising fluorescent or enzymatic detection labels or epitope tags for binding of labeled secondary antibodies. Such pY binding compositions of the invention may be utilized in the detection and/or quantification of proteins comprising phosphotyrosine residues. Exemplary applications include Western blotting, immunofluorescence assays, flow cytometry applications, immunoprecipitations, and pY proteomics analyses. In a general method of the invention, a pY binding composition of the invention is applied to a sample, wherein the pY binding composition is configured as a detection agent and is applied to the sample under conditions suitable for binding of the pY binding composition to phosphotyrosine residues present in the sample. Following application to the sample, the sample is analyzed for bound pY binding agents, for example by fluorescence microscopy, allowing quantification, localization, or other analyses to be performed. The sample may comprise a biological sample, e.g. blood, cells, serum, tissues (e.g. sections), or other biological material.

In another embodiment, the pY binding composition of the invention is configured as a therapeutic agent, for example, targeted to phosphotyrosine-bearing proteins associated with aberrant signaling activity, for example, to inactivate or inhibit a target phosphorylated protein. In some implementations, binding of the pY binding composition to the phosphotyrosine-containing target interferes with signaling pathways mediated by the target, i.e. it acts as an inhibitor. In other therapeutic applications, the pY binding composition is configured as a drug delivery construct, comprising a pY binding composition conjugated to a drug. In other therapeutic applications, the pY binding composition is configured as a cell killing agent, comprising functional groups that kill cells, e.g. cytotoxic agents. In the therapeutic methods of the invention, the pY binding composition is administered in a therapeutically effective amount to a subject in need of treatment for a condition associated with moieties comprising the targeted phosphotyrosines, wherein binding of the pY agent to targeted phosphotyrosines achieves a therapeutic effect.

EXAMPLES

Example 1. Engineering Improved Anti-Phosphotyrosine Antibodies Based on Immuno-Convergent Binding Motif Phosphotyrosine (pY) is one of the most highly studied posttranslational modifications that is responsible for tightly regulating many signaling pathways in eukaryotes. Pan-specific pY antibodies have emerged as powerful tools for understanding the role of these modifications. Nevertheless, structures have not been reported for pan-specific pY antibodies, greatly impeding the further development of tools for integrating this ubiquitous posttranslational modification using structure-guided designs. Here is described the first crystal structures of two widely utilized pan-specific pY antibodies, PY20 and 4G10. The two antibodies, although developed independently from animal immunizations, have surprisingly similar modes of recognition of the phosphate group, implicating a generic binding structure among pan-specific pY antibodies. Sequence alignments revealed that many pY binding residues are predominant in the mouse V germline genes, which consequently led to the convergent antibodies. Based on the convergent structure, a phage display library was designed for lengthening the CDR-L3 loop with the aid of computational modeling. Panning with this library resulted in a series of 4G10 variants with 4 to 11 fold improvements in pY binding affinities. The crystal structure of one improved variant showed remarkable superposition to the computational model, where the lengthened CDR-L3 loop creates an additional hydrogen bond indirectly bound to the phosphate group via a water molecule. The engineered variants exhibited superior performance in Western blot and immunofluorescence.

Results

Crystal structures of PY20 and 4G10 Fabs complex with sulfate group. To facilitate the engineering of improved pY probes, the pY antibody crystal structure was solved in complex with a phosphopeptide in order to understand the mechanism by which it recognizes pY. Two widely utilized pY antibodies, PY20 and 4G10, were recombinantly expressed using *E. coli* in a Fab format. Co-complex crystallographic screens were set up with the purified Fab mixed with a 3-mer synthetic peptide LpYL. Initial attempts were impeded by protein aggregates that failed to generate good-quality crystals possibly due to the low stability of the antibodies. The 4D5 human antibody scaffold from traztuzumab is very stable (Tm ~82° C.), and it has previously been found that antibodies derived from it are very stable. Thus, it was hypothesized that increased stability would be imparted in humanized PY20 and 4G10 by grafting their CDRs on to the 4D5 scaffold. Indeed, the humanized Fabs PY20$^{4D5}$ and 4G10$^{4D5}$ exhibited great thermostability with $T_m$ at 76° C. and 80° C., respectively, as compared to the parental 4G10's $T_m$ at 65° C. Importantly, an ELISA assay confirmed that both PY20$^{4D5}$ and 4G10$^{4D5}$ had preserved pY binding affinity and specificity. The co-crystallizations of PY20$^{4D5}$/LpYL and 4G10$^{4D5}$/LpYL successfully generated crystals with good diffraction properties. Unfortunately, the crystal structures of both the PY20$^{4D5}$ and 4G10$^{4D5}$ Fab fragments did not reveal any electron density for the LpYL peptide despite the fact that the Fab fragment could be well refined. Instead, there was a tetrahedron-like density engulfed in the CDR pocket at the same position of PY20$^{4D5}$ and 4G10$^{4D5}$. It was observed that all the crystallization hits grown in buffer containing either phosphate or sulfate salts, which possibly outcompeted the pY peptide binding. Indeed, a sulfate group modeled into the electron density was well coordinated by multiple hydrogen bonds and salt bridges. Interestingly, the proposed sulfate binding sites are very similar between PY20$^{4D5}$ and 4G10$^{4D5}$. Both structures use T33$_H$ and H35$_H$ from the stem region of CDR-H1 and R95$_H$ from the stem region of CDR-H3 to bind the sulfate ion. The major difference is that 4G10$^{4D5}$ has an additional interaction to the phosphate from R96$_L$ of the CDR-L3 loop. This observation is consistent with kinetic binding data, where 4G10$^{4D5}$ shows a tighter binding affinity to pY compared to PY20$^{4D5}$. To further test our hypothesis that the sulfate ion is a competitive inhibitor of pY, binding experiments were performed in the presence of excess sulfate ion and found that the pY peptide no longer bound to the antibody.

Crystal structure of 4G10 Fab complex with the pY peptide. Since 4G10$^{4D5}$ is a superior pY binder to PY20$^{4D5}$, a more extensive co-crystallization screening was performed in the absence of sulfate or phosphate ions with 4G10$^{4D5}$/LpYL in hopes of obtaining crystals with the LpYL bound. Indeed, such a condition was achieved and good diffraction of the crystals was acquired to a resolution of 2.3 Å. The crystal structure showed a clear electron density for the first two residues of the LpYL peptide bound in the 4G10$^{4D5}$ CDR pocket. The phosphate group of pY is deeply buried in the stem region of the CDRs at the same position where the sulfate ion was observed in the previous PY20$^{4D5}$ and 4G10$^{4D5}$ structures. There are four important features in the 4G10$^{4D5}$/LpYL structure that appear to confer the pan-specificity of pY substrates. (i) The residues R96$_L$, T33$_H$, H35$_H$, and R95$_H$ form direct hydrogen bonds or salt bridges to the phosphate group of pY. (ii) There are three water molecules surrounding the pY residue that form hydrogen bonds with the phosphate group, and each of them mediates the hydrogen-bond interactions between the 4G10$^{4D5}$ antibody and the pY residue. The residues Y91$_L$ and Y100$_H$, which pack as a parallel displaced π-π stacking, form hydrogen bonds to two water molecules individually. The third coordinated water molecule lies on top of the tyrosine ring and is stabilized by three hydrogen bonds, two from the phosphate group and the backbone carboxyl of the pY residue, respectively, and one from the N52$_H$ of the antibody. (iii) The residues G55$_H$ and G56$_H$ form a "seat" that is shape complementary to the backbone of the pY-proceeding residue. The G55$_H$ has the torsion angles (phi=95.8, psi=−15.8) that are forbidden for all amino acids except glycine. The position 56 could only accommodate a glycine without creating steric clashes to the pY peptide. (iv) The proceeding residue of pY points the side chains toward the solvent, i.e. it does not interact with the antibody. The following residue of pY does not show a clear electron density, implying no static interactions to the antibody. This explains the pan-specificity of 4G10 because the antibody only interacts with the pY residue, but not the neighboring ones. Surprisingly, there are no π-π stacking or cation-π interactions between the antibody and the pY residue. The tyrosine simply acts as a bridge to extend the phosphate group into the deep binding pocket. This confers the pY specificity of 4G10$^{4D5}$ over pS and pT, because pS and pT are too short to reach the phosphate binding site. Intriguingly, among the nine critical residues mentioned above, only one residue (G55$_H$) is at the loop structure, whereas the other eight residues (Y91$_L$, R96$_L$, T33$_H$, H35$_H$, N52$_H$, G56$_H$, R95$_H$, Y100$_H$) that mediate phosphate binding are located on the β-strands that are either at or very close to the framework regions. Overall, the 4G10$^{4D5}$ structure has a fairly deep and sophisticated binding site that provides eight hydrogen bonds and/or salt bridges directly or indirectly bound to the phosphate group.

Structure-guided design to improve the 4G10/pY binding. Next it was sought to leverage the structural insights gained from the crystallographic data to further engineer 4G10 to improve its properties as a detection reagent. Based on the PY20$^{4D5}$/sulfate structure, a single mutant D59N was designed, which was hypothesized might improve the affinity by replacing the repulsive interaction between D59 and pY with a hydrogen bond between N59 side chain amide and pY. The kinetic binding assay showed that the D59N mutant indeed improved the affinity to 1 μM, which was approximately 2-fold superior to PY20$^{4D5}$ but still inferior to 4G10$^{4D5}$. Next, single mutants of 4G10$^{4D5}$ were designed in an attempt to introduce π-π stacking or cation-π interaction to the pY residue according to the 4G10$^{4D5}$/LpYL structure. However, all eight single mutants (N52F, N52K, N52R, N52H, I58F, I58K, I58R, I58H) significantly diminished the pY binding.

Given the limited space at positions 52$_H$ and 58$_H$, it was speculated that the diminished binding was caused by the steric clashes to the pY peptide. Solvent-accessible surface area (SASA) analysis showed that the pY group is well packed by 4G10$^{4D5}$ except that one side of pY is more solvent-exposed. It was aimed to create extra affinity from this side by more aggressive engineering. A close inspection of the CDRs revealed that a lengthened CDR-L3 loop might contribute additional interactions to the pY group from the solvent-exposed side. Computational tools were used to model various insertions between the 92$_L$ and 94$_L$ residues. It was found that an insertion of three or four residues might provide new contacts to the pY group. For example, based on the modeling, a 3-residue insertion with a serine at the C-terminus could create an additional hydrogen bond to the water molecule mediating to the phosphate.

A 4G10$^{4D5}$ phage display library was prepared with the CDR-L3 lengthened by 0 to 4 residues using degenerate codons. The library was panned against a pY peptide with three glycines on the flanking regions (GGGpYGGG, SEQ ID NO: 87). Five rounds of selections with decreased concentrations of the pY peptide (1 μM, 300 nM, 100 nM, 30 nM, and 10 nM) were performed. Good enrichment ratios were obtained in each round comparing the pY peptide and its non-phosphorylated counterpart titters. 92 clones were selected from rounds 3 to 5 (~30 clones from each round) and sequenced. The sequencing results showed that the 3-residue insertion clones were the most predominant (84/92), whereas the 0, 1, 2, and 4-residue insertions only account for 0, 0, 1, and 7 clones, respectively. Phage ELISA assays were employed to evaluate the pY binding specificity and affinity. The direct ELISA assay showed that all clones retained exquisite pY selectivity over non-phosphorylated tyrosine. More than 60 clones showed improved affinity compared to the parental 4G10$^{4D5}$ in a competitive ELISA assay, where a soluble pY peptide at 200 nM was used as the competitor. Based on the competitive ELISA results, the top 12 clones were selected (all were 3-residue insertions) and expressed them recombinantly as Fabs for affinity measurements. The sequences of the top 12 clones could be grouped into two motifs: XX(T/S)S (SEQ ID NO: 89, 6 clones) and XXXG (SEQ ID NO: 86, 6 clones). The biolayer interferometry measurements showed that all 12 clones exhibited better pY binding affinity compared to the parental 4G10$^{4D5}$. Whether the choices of the 4D5 scaffold or the 4G10 scaffold would affect the binding affinity was further tested. 6 clones were picked from the top 12 variants and grafted their CDR-L3 sequence back to the parental 4G10 scaffold. It was found that the variants in the 4G10 and 4D5 scaffolds have comparable binding affinities. Overall, the 18 4G10 variants validated showed better pY binding affinity compared to the parental 4G10$^{4D5}$ ranging from 4.3 to 11.2 fold improvement.

Structural elucidation of the improved pY antibody. In order to better understand the improved affinity of the CDR-L3 lengthened variants, the crystal structure of the 4G10-S5$^{4D5}$ co-complex was solved with the LpYL peptide. The 4G10-S5$^{4D5}$ structure keeps the LpYL binding and the three surrounding water molecules the same way as the 4G10$^{4D5}$. In addition, the last residue of the LpYL peptide was well defined in the electron density map. Like the residue proceeding the pY, the residue following the pY also points the side chain toward the solvent, thus making no interactions with the antibody. The serine at the position 95A$_L$ from the lengthened L3 creates a new hydrogen bond to the water molecule that is also hydrogen bonded by Y91$_L$ and the pY phosphate. Furthermore, the CDR-L3 forms a loop that is structurally fixed by a hydrogen bond between S92$_L$ and T95$_L$. This hydrogen bond, although not directly contributing to the pY binding, stabilizes the conformation of CDR-L3 loop and keeps S95A$_L$ in close proximity to the water molecule responsible for pY binding. The 4G10-S5$^{4D5}$/pY structure is well predicted by the computational model. In the in silico models where one hundred 3-residue-insertion CDR-L3 loops were built, there are two canonical conformations with one energy much more favorable than the other. Indeed, the 4G10-S5$^{4D5}$/pY crystal structure superimposed with the energetically-favorable conformation of CDR-L3 in the model.

Engineered pY antibodies show superior performance in immunoaffinity applications. The performance of the parental 4G10 and the affinity-improved variants was compared in two experimental applications, pY Western blot and pY immunofluorescence. For the pY Western blot experiments, the whole cell lysate of Jurkat cells with or without the pre-treatment of pervanadate (a phosphotyrosine phosphatase inhibitor) was used. Consistent with previous observations, due to the tight regulation of pY modifications in cells, there were hardly any pY signals detected in the lysate without the pervanadate pre-treatment, reflecting dominant tyrosine phosphatase activity in cells. The lack of signal verifies that the 4G10 antibody and the engineered variants show very little general protein cross-reactivity in the whole cell lysate. Conversely, the lysates pre-treated with pervanadate show multiple bands across a wide range of molecular weights, reflecting the pY pan-specificity of 4G10 and its engineered variants. Notably, there are many bands that are hardly detected by 4G10 but readily detected by the engineered variants, particularly in the range of ~25-55 kD. The signal improvement in this molecular weight range is up to 7.2 fold compared 4G10-S5$^{4G10}$ to the parental 4G10. In terms of the overall signal intensity and number of bands detected, the best variants for the Western blot application are 4G10-G1$^{4G10}$, 4G10-G6$^{4D5}$, and 4G10-S5$^{4G10}$, with the overall intensity improved by ~200% compared to the parental 4G10.

It was next sought to compare the immunofluorescence sensitivity for the parental 4G10 and the 3 best variants from the Western blot results. HeLa cells with or without the pervanadate pre-treatment were fixed and immuno-stained. Similar to the Western blot experiments, the cells without pervanadate pre-treatment did not show any detectable immunofluorescence (data not shown), indicating the tight pY regulation under physiological conditions and the absence of antibody non-specific binding. For cells pre-treated by pervanadate, the parental 4G10 showed moderate immunofluorescence in the cytoplasm region, whereas two engineered variants, 4G10-G6$^{4D5}$ and 4G10-S5$^{4G10}$ exhibited as much as 250% brighter signals in comparison. The 4G10-G1$^{4G10}$ variant, however, only showed comparable intensity with the parental 4G10, despite of its superior performance in the Western blot experiment. Collectively this data illustrates that the engineered variants exhibit superior performance to the parental 4G10 in both pY Western blot and pY immunofluorescence experiments. One particular variant, 4G10-S5$^{4G10}$, showed the best signals in both applications.

DISCUSSION. Two widely utilized pan-specific pY antibodies, PY20 and 4G10, were successfully grafted onto a highly stable scaffold 4D5 and their crystal structures solved. Surprisingly, PY20 and 4G10 share nearly the same mode of binding for the phosphate group despite being raised from independent animal immunization origins. Another intriguing feature revealed by the structures is that all the binding residues, including those have direct or indirect interactions to the pY residue, are located in the stem regions (mostly in β-strand structure) of CDRs, but not in the middle of CDR loops. Therefore, the binding site is rather static and does not require a recognition-induced conformational change for binding. Overall, the structure harbors a deep but well-exposed and electrostatically complementary binding site for pY binding. Surprisingly, there are no π-π interactions or cation-π interactions to the aromatic ring of pY. The pY specificity comes from the depth of the binding site, which can not be reached by pS or pT because of their short side chains. The structures also reveal that neighboring residues of pY do not directly interact with the antibody, therefore conferring the pY pan-specificity. This is in contrast to other natural pY binding proteins, such as SH2 domains. SH2 domains recognize their pY substrates with strong sequence preference. There are two binding pockets of SH2 domains, namely the pY binding pocket and the peptide pocket. Similar to the 4G10 paratope, the SH2 pY binding pocket contains cationic residues (typically two arginine and one histidine) critical for phosphate coordination. However, the binding of this pocket alone is relatively weak and only contributes roughly half of the substrate binding energy. The other half binding energy is provided by the extended peptide groove, which recognizes the residues C-terminal to the pY group. This pocket is highly variable among the SH2 domains in order to achieve different peptide sequence specificity. Inspired by the SH2 domains, generalized recombinant antibody scaffolds were produced for pS, pT, and pY peptide binding using CDR-H2 as the phosphate pocket and CDR-L3/CDR-H3 as the peptide pocket. While the pS and the pT scaffolds were highly specific to their cognate peptides, the pY scaffold did not show strong preference for pY over non-phosphorylated tyrosine. The structure showed little burial of the pY side chain in CDR-H2.

Ruff-Jamison et al. performed a systematic comparison of several antibodies generated by mouse immunization using pY antigens. Based on the sequence similarity, it was deduced that two pairs of antibodies, PY2/PY54 and PY20/PY69, arose from the same ancestral clones, respectively, and diverged later by somatic mutations. PY42 and 129 IgM likely arose from independent clones. Of these six clones, they found common and distinct features in all six CDRs at the sequence level. It was not clear if the sequence consensus implicates a similar pY binding structure shared by all six antibodies, and if so, which consensus residues are responsible for the pY binding. With the PY20 and 4G10 structures solved here, the sequence alignment were re-analyzed and it was discovered that most residues critical for the pY binding in the structures are indeed conserved across the PY clones and 129 IgM. The conserved residues could be structurally categorized into 3 types: (i) direct binding residues to pY (magenta); (ii) a hydrogen bond network around pY mediated by water molecules (yellow); (iii) the GG motif in CDR-H2 (green). All antibodies have at least two residues in each type with exception to 129 which lacks the residues for binding to water molecules. Consistently, 129 is the weakest pY antibody with the binding affinity 2-3 order of magnitude lower than the PY clones. The conservation across different types of binding residues implies that these antibodies likely resemble the same structure for pY binding in spite of their different clonal origins.

The structural convergence among multiple independent pY antibodies is rather surprising given that VDJ recombination and somatic hypermutation is a highly variable and random process. Since the immuno-convergent pY binding site is composed of many residues from the β-strands in the framework region, and not the CDR loops, it was suspected that some of those residues critical to the pY binding might pre-exist in the mouse V germline genes prior to somatic hypermutation. Indeed, sequence alignments to the mouse V germline database (ABG database) revealed that six ($Y91_L$, $T33_H$, $H35_H$, $N52_H$, $G55_H$, $G56_H$) out of nine residues critical for pY binding in 4G10 were predominant in the consensus sequences of mouse VH and Vk germline genes. The $Y91_L$ residue was found in 9 of 67 Vk germline genes, and the $T33_H$, $H35_H$, $N52_H$, $G55_H$, and $G56_H$ residues were found in 10, 83, 54, 135, 40 of 185 VH germline genes, respectively. Furthermore, there are 2 VH germline genes that simultaneously contain all these 5 critical residues, whereas 14 and 33 VH germline genes contain 4 and 3 of the 5 critical residues, respectively. Therefore, it is hypothesized that the immuno-convergence of pY binding residues arose from pre-existing mouse germline genes, rather than independent solutions through somatic hypermutation. This immuno-convergence, i.e. a particular antigen immunization induces similar sequences of antibodies from diverse genetic backgrounds, is a longstanding observation in both human and mouse. For instance, it has been long known that immunization with simple hapten antigens, such as arsenate (Ars) or 4-hydroxy-3-nitrophenylacetyl (NP), would induce essentially identical antibodies from different mice. The molecular mechanism behind this convergence was not clear, but it is generally assumed that the antibody repertoire has very limited solutions to this kind of antigen. The structural data and the sequence analysis herein provide an alternative explanation. Several pre-existing V germline genes were found encoding a set of residues favorable for pY antigen binding outside the CDR region. These genes would then be quickly affinity-matured and therefore lead to the convergent antibodies. It is hypothesized that pre-disposed binding residues in the V germline genes are more likely happened to simple antigens, such as pY and small haptens. In addition to haptens, simple epitopes from complex antigens, such as immunodeficiency virus, dengue virus, and influenza virus, have also resulted in convergent immunoglobulins. The convergence would be especially profound if many germline genes share consensus residues attributing to the antigen binding, such as the case of pY.

Traditional in vitro antibody affinity maturation often relies on random/rational mutagenesis of the CDRs without altering the loop lengths. Here, a different approach was adopted, in which the CDR-L3 loop was lengthened based on the 4G10/pY co-complex structure, and affinity-improved variants were successfully created. This approach leveraged the combinational power of computational loop modeling and experimental phage display selection. One of the improved variants was structurally validated with X-ray crystallography and showed virtually superimposable structure with the design model. The advancement of computational tools has enabled accurate loop modeling in several examples, including building long loops with high resolution, altering enzyme specificity, and predicting antibody hypervariable conformations. Herein was showed that the loop modeling could also be utilized as a useful tool for antibody affinity maturation. The affinity-improved variants exhibited better performances than the parental 4G10 in two pY applications, Western blot and immunofluorescence.

This work provides, for the first time, structural insights into the mechanism of pY recognition of the most widely used antibodies in biological research. It was found that pY antibodies derived from independent immunization share a convergent pY binding site. Based on the convergent pY antibody structures, a hypothesis is proposed that explains the long observed convergent immunoglobulin responses: the mouse V germline genes share predominant antigen-binding residues, and therefore little affinity maturation by means of V gene hypermutation is required for raising high-affinity antibodies. Furthermore, herein was demonstrated how the convergent pY antibody structures can be harnessed to build improved next generation tools for better pan-specific detection and isolation of the pY proteome.

Methods

Construct preparation, protein expression, and purification. All the Fabs were constructed in a dual-expression vector that expresses the light chain and the heavy chain with the pelB and the stII signal peptides, respectively, for the periplasm expression. A C-terminal 6×His tag (SEQ ID NO: 105) was put in the heavy chain. The CDR grafting was achieved by Kunkel cloning. The Fabs were expressed using C43(DE3) E. coli strain at 30° C. for approximately 20 hours with 1 mM IPTG induction. The cells were harvested by centrifugation and lysed using B-PER lysis buffer. For the 4D5 scaffold Fabs, the lysate was incubated at 60° C. for 20 minutes and centrifuged to remove the inclusion body. The Fabs were purified by Ni$^{2+}$-NTA resin and buffer exchanged in TBS buffer for further characterization.

X-ray crystallography. The Fabs were concentrated to 15 mg/mL using MWCO 30 kDa Amicon Ultra centrifugal filter units. The LpYL peptide was purchased from Sino Biological with HPLC purification. The Fab and the peptide were mixed at 1:5 molar ratio and set up for crystallographic conditions using hanging-drop vapor diffusion at room temperature. The PY20$^{4D5}$ crystals were grown in 20% PEG4000 and 0.336M ammonium sulfate, pH 6.0. The 4G10$^{4D5}$ crystals were grown in 20% PEG4000, 0.2M ammonium sulfate, and 0.1M sodium acetate at pH 5.5. The 4G10$^{4D5}$/LpYL co-complex crystals were grown in 20% PEG3350, 0.2M potassium/sodium tartrate, and 0.1M Bir-tris propane at pH 6.5. The c310/LpYL co-complex crystals were grown in 26% PEG3350, 0.1M Bis-Tris, and 0.16M ammonium acetate at pH 6.0. All crystals were soaked in 15% glycerol in the well solution and flash cooled by liquid nitrogen. Diffraction data were collected at the Advanced Light Source Beamline 8.3.1 at the Lawrence Berkeley National Laboratory. iMosflm and XDS were used for data processing. The diffraction phases were obtained through molecular replacement using PHENIX, initially using the CDR-trimmed Fab structure in PDB 1BJ1 and later using the 4G10$^{4D5}$ structure. Ellipsoidal truncation of the PY20$^{4G5}$ dataset was performed on the Diffraction Anisotropy Server (University of California, Los Angeles) to correct for the strong anisotropy along the b direction and significantly improved the electron density map. Further refinement and real space adjustment were done with PHENIX and Coot, respectively.

Computational modeling Triad computational protein design suite was employed for loop modeling of the 4G10$^{4D5}$ CDR-L3 loop. The 4G10$^{4D5}$/LpYL co-complex structure was used as input. The 92$_L$ and 94$_L$ residues were fixed as anchor points, and the 93$_L$ residue was replaced with 1, 2, 3, or 4 alanines or glycines. During the loop modeling, the nearby residues are repacked, and the overall structure is energy minimized. For each loop length, 100 lowest energy conformations were output. Based on the Ala/Gly loop, the loop sequence was designed to maximize the binding affinity to the LpYL peptide.

Phage library construction. The L3 library was constructed by randomized oligonucleotides using degenerate codons. The phagemid that contained the 4G10$^{4D5}$ gene was double digested by PstI and KpnI, which are located on the two flanking sides of the CDR-L3, respectively. Five pairs of forward and reverse oligonucleotides that construct different lengths of L3 were purchased from Integral DNA Technology. The oligonucleotides were 5' phosphorylated by T4 polynucleotide kinase at 37° C. for 1 hour. An equimolar mixture of the forward and the reverse oligomers was heated to 95° C. for 10 min and gradually cooled down to room temperature. The annealed dsDNA was ligated into the PstI/KpnI digested phagemid and transformed into SS320 electro-competent cells. After one hour recovery at 37° C., the cells were expanded into 500 mL 2xYT with 50 ug/mL carbenicillin. The M13KO7 helper phage was added to the culture at MOI=10 when OD600=0.6. The culture was grown for approximately 20 hours with 250 rpm shaking at 37° C. Next day, the cells were pelleted by centrifugation. The phage was precipitated from the supernatant by adding ⅕ volume of 20% PEG8,000 and 2.5M NaCl. The phage library was resuspended in TBS buffer with 50% glycerol and 2 mM EDTA and stored at −20° C.

Phage display selection. All phage selections were done according to established protocols. Briefly, the L3 phage library was first enriched by protein L magnetic beads to deplete non-displayed or truncated Fab phage. The enriched library was then selected against a biotinylated peptide GGGpYGGG (SEQ ID NO: 87) immobilized on streptavidin-coated magnetic beads. A biotinylated peptide GGGYGGG (SEQ ID NO: 88) was used for library clearance and enrichment tests. In total, five rounds of selections were performed with decreasing amounts of GGGpYGGG (SEQ ID NO: 87) peptide (1M, 300 nM, 100 nM, 30 nM, and 10 nM). After each round, the phage titer was determined according to standard protocols. Briefly, the acid-eluted phage was serially diluted and added to mid-log phage XL1-Blue E. coli. The infected culture was incubated for 20 min at room temperature on an orbital shaker. The cells were spotted on LB-agar plates with carbenicillin and incubated overnight at 37° C. The enrichment was determined by comparing the phage titers of GGGpYGGG (SEQ ID NO: 87) and GGGYGGG (SEQ ID NO: 88) selections.

Phage ELISAs. ELISAs were performed according to standard protocols. Briefly, a single colony from the phage selection was picked into 1 mL 2xYT with 50 µg/mL carbenicillin, 5 µg/mL tetracycline, and 10$^{10}$ M13KO7 helper phage particles. The culture was grown for approximately 20 hours at 37° C. in a shaking incubator. The overnight culture was spun down to pellet the cells. The phage supernatant was diluted 5 fold in TBS buffer with 0.05% Tween-20 and 0.2% BSA for ELISA. 384-well MAXISORP™ plates were coated with NEUTRA/AVIDIN™ (5 µg/mL) overnight at 4° C. 200 nM of biotinylated GGGpYGGG (SEQ ID NO: 87) or GGGYGGG (SEQ ID NO: 88) was captured by NEUTRA/AVIDIN™ in the MAXISORP™ plate for 30 min at room temperature. The plate was washed three times and loaded with diluted phage supernatant for 30 min. In the case of competitive ELISA, the diluted phage supernatant was first incubated with 200 nM biotinylated GGGpYGGG (SEQ ID NO: 87) before loading on the plate. The plates were washed three times and loaded with anti-M13 horseradish peroxidase (HRP) conjugate for 15 min. The plate was washed three times and detected by TMB substrate at 450 nm.

Binding kinetics. Biolayer interferometry data were measured using an OCTET RED384™ (ForteBio). Biotinylated peptides GGGpYGGG (SEQ ID NO: 87) or GGGYGGG (SEQ ID NO: 88) were immobilized on the streptavidin (SA) biosensor. Purified Fabs were used as analyte in the solution. TBS with 0.05% Tween-20 and 0.2% BSA was used for all diluents and buffers. A 1:1 monovalent binding model was used to fit the kinetic parameters ($k_{on}$ and $k_{off}$).

Western blot Jurkat cells were pre-treated with 0.1 mM freshly activated pervanadate for 15 minutes at 37° C. The cells were harvested and lysed using RIPA buffer containing 1 mM EDTA and protease inhibitor cocktails. The lysate was briefly sonicated and quantified by BCA assay. 10 µg of the protein lysate was loaded into each well and run on a 4-20% SDS-PAGE. The gel was transferred to a PVDF membrane. The membrane was briefly washed and blocked with Odyssey TBS blocking buffer at 4° C. overnight. The membrane was then incubated with the pY Fab at 200 nM at room temperature for 30 min followed by 6×His tag antibody conjugated with DYLIGHT 680™. The membrane was imaged with LI-COR system.

Immunofluorescence The HeLa cells were pre-treated with 0.1 mM freshly activated pervanadate for 15 minutes at 37° C. The cells were fixed by adding −20° C. methanol for 5 minutes followed by air-drying. These cells were rehydrated in TBS with 200 nM pY Fab at room temperature. After washing three times with TBS, the fluorescence staining was performed by adding 6×His tag antibody conjugated with DYLIGHT 680™ and DAPI. The immunofluorescence images were taken using a Zeiss microscope with oil immersion objectives.

Data availability Atomic coordinates and structure factors have been deposited in the Protein Data Bank under accession codes PDB 6DEZ (PY20$^{4G5}$ complex with sulfate), 6DF0 (4G10$^{4D5}$ complex with sulfate), 6DF1 (4G10$^{4D5}$ complex with pY peptide), and 6DF2 (4G10-S5$^{4D5}$ complex with pY peptide).

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A phosphotyrosine-binding composition, comprising an antibody, or phosphotyrosine-binding fragment thereof, wherein the antibody or antibody fragments comprises:
a body scaffold comprising heavy and light chain sequences;
a CDR L1 sequence comprising SEQ ID NO: 24;
a CDR L2 sequence comprising SEQ ID NO: 25;
a CDR H1 sequence comprising SEQ ID NO: 26;
a CDR H2 sequence comprising SEQ ID NO: 27;
a CDR H3 sequence comprising SEQ ID NO: 28; and
a CDR L3 sequence comprising
a sequence selected from the group consisting of: SEQ ID NO: 6-SEQ ID NO: 23.

2. The phosphotyrosine binding composition of claim 1, wherein
the antibody or fragment thereof comprises a whole antibody, a Fab, a Fab', a F(ab)$_2$, or a scFv.

3. The phosphotyrosine binding composition of claim 1, wherein
the antibody or fragment thereof comprises one or more functional moieties.

4. The phosphotyrosine binding composition of claim 3, wherein
the one or more functional moieties comprises an affinity tag, a fluorescent label, or an epitope for binding by secondary antibodies.

5. The phosphotyrosine binding composition of claim 1, wherein
the CDR L3 sequence comprises SEQ ID NO: 15.

6. The phosphotyrosine binding composition of claim 1, wherein
the CDR L3 sequence comprises SEQ ID NO: 22.

7. The phosphotyrosine binding composition of claim 1, wherein
the CDR L3 sequence comprises SEQ ID NO: 10.

8. The phosphotyrosine binding composition of claim 1, wherein
the CDR L3 sequence comprises SEQ ID NO:12.

9. The phosphotyrosine binding composition of claim 1, wherein
the CDR L3 sequence comprises SEQ ID NO: 14.

10. The phosphotyrosine binding composition of claim 1, wherein
the antibody, or phosphotyrosine binding fragment thereof, comprises:
a light chain comprising a sequence of at least 95% sequence identity to SEQ ID NO: 39, wherein the CDR L3 sequence thereof comprises a sequence selected from the group consisting of SEQ ID NO: 6-SEQ ID NO: 23; and
a heavy chain comprising a sequence of at least 95% sequence identity to SEQ ID NO: 43.

11. The phosphotyrosine binding composition of claim 10, comprising
a light chain comprising a sequence of at least 95% sequence identity to SEQ ID NO: 40; and
a heavy chain comprising a sequence of at least 95% sequence identity to SEQ ID NO: 43.

12. The phosphotyrosine binding composition of claim 10, comprising
a light chain comprising a sequence of at least 95% sequence identity to SEQ ID NO: 41; and
a heavy chain comprising a sequence of at least 95% sequence identity to SEQ ID NO: 43.

* * * * *